United States Patent
Dumont et al.

(10) Patent No.: US 12,377,214 B2
(45) Date of Patent: Aug. 5, 2025

(54) SYSTEMS AND METHODS FOR CONTROLLED DELIVERY OF ANALGESIC AND HYPNOTIC AGENTS

(71) Applicant: The University of British Columbia, Vancouver (CA)

(72) Inventors: Guy Dumont, Vancouver (CA); Klaske Van Heusden, Vancouver (CA); Mark Ansermino, Vancouver (CA)

(73) Assignee: NeuroWave Systems Inc., Cleveland, OH (US)

( * ) Notice: Subject to any disclaimer, the term of this patent is extended or adjusted under 35 U.S.C. 154(b) by 1000 days.

(21) Appl. No.: 17/398,370

(22) Filed: Aug. 10, 2021

(65) Prior Publication Data

US 2022/0031945 A1 Feb. 3, 2022

Related U.S. Application Data

(63) Continuation of application No. 16/149,575, filed as application No. PCT/IB2017/052121 on Apr. 12, 2017, now Pat. No. 11,116,897.

(60) Provisional application No. 62/324,208, filed on Apr. 18, 2016.

(51) Int. Cl.
| | |
|---|---|
| *A61M 5/172* | (2006.01) |
| *A61B 5/00* | (2006.01) |
| *A61M 19/00* | (2006.01) |
| *A61M 21/00* | (2006.01) |
| *A61M 5/14* | (2006.01) |

(52) U.S. Cl.
CPC .......... *A61M 5/172* (2013.01); *A61B 5/4821* (2013.01); *A61M 19/00* (2013.01); *A61M 21/00* (2013.01); *A61B 5/7203* (2013.01); *A61M 5/14* (2013.01); *A61M 2230/08* (2013.01)

(58) Field of Classification Search
CPC ........ A61M 2230/08; A61M 2230/005; A61M 19/00; A61M 21/00; A61M 5/14; A61M 5/172; A61B 5/4821
See application file for complete search history.

(56) References Cited

U.S. PATENT DOCUMENTS

2012/0095437 A1\* 4/2012 Hemmerling ....... A61M 5/1723
604/503

FOREIGN PATENT DOCUMENTS

WO WO-2008086624 A1 \* 7/2008 ........... A61B 5/0205

\* cited by examiner

*Primary Examiner* — Nilay J Shah
(74) *Attorney, Agent, or Firm* — Brian Kolkowski

(57) ABSTRACT

The invention involves the administration of clinical anesthesia. Particular embodiments provide systems and methods for controlled delivery of a combination of an analgesic agent and a hypnotic agent. More specifically, the invention involves closed-loop control systems/methods for automatically controlling the administration of a combination of a hypnotic agent and an analgesic agent in a clinical anesthesia setting which incorporate feedback based on one or more indirect measures/indicia of analgesia. The invention further includes such control systems/methods that account for limitations of such indirect measures/indicia of analgesia.

20 Claims, 7 Drawing Sheets

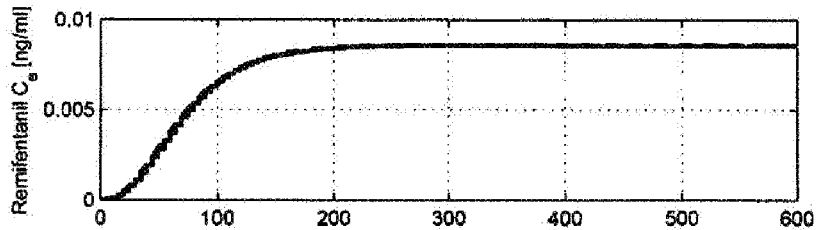
FIGURE 10A
FIGURE 10B
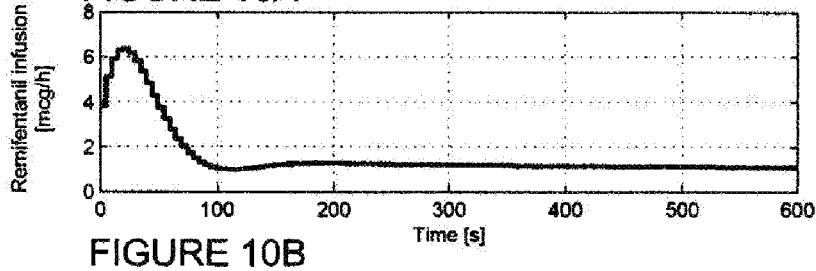
FIGURE 11A
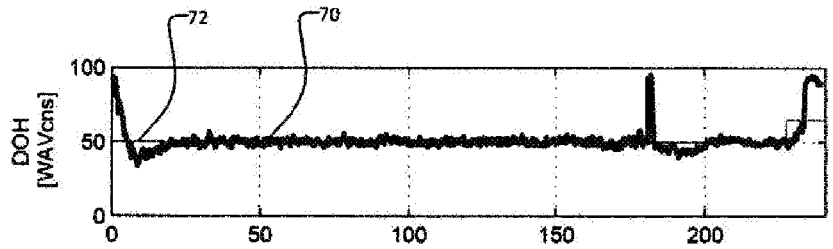
FIGURE 11B
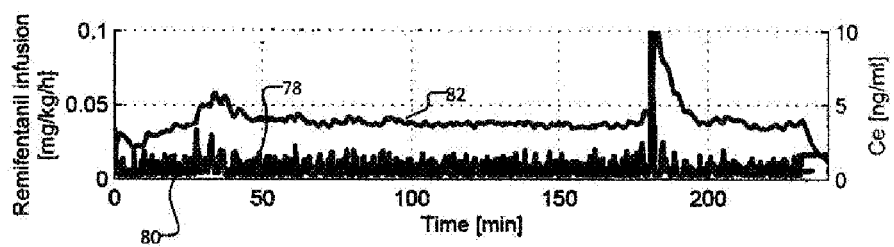
FIGURE 11C

SYSTEMS AND METHODS FOR CONTROLLED DELIVERY OF ANALGESIC AND HYPNOTIC AGENTS

CROSS-REFERENCE TO RELATED APPLICATIONS

This application is a continuation of U.S. patent application Ser. No. 16/149,575 which was filed on Oct. 2, 2018, and which was filed under 35 U.S.C. § 371 as a national stage application of international application serial no. PCT/IB2017/052121, which was filed on Apr. 12, 2017, and which claimed priority to U.S. Provisional Patent application Ser. No. 62/324,208, which was filed on Apr. 18, 2016. The specifications and drawings of each of the above applications are hereby incorporated by reference in their entirety.

TECHNICAL FIELD

The invention relates to administration of clinical anesthesia. Particular embodiments provide systems and methods for controlled delivery of a combination of an analgesic agent and a hypnotic agent.

BACKGROUND

Clinical anesthesia typically involves administering a combination of drugs comprising an anesthetic or hypnotic agent (to suppress consciousness) and an analgesic agent (to suppress response to painful stimuli). A typical, although non-limiting, hypnotic agent is propofol. A typical, although non-limiting analgesic agent is remifentanil. Other drugs, such as a muscle relaxant, may also be combined with the hypnotic agent and the analgesic agent. Insufficient drug dosing may lead to awareness or perceived pain (in the subject being anesthetized) as well as potentially harmful responses to nociceptive stimulation. Overdosing may lead to cardiovascular collapse or cause the subject to stop breathing. Consequently, in typical clinical settings, an anesthesiologist closely monitors the physiological state of the subject and adjusts drug infusion rates accordingly.

The time and attention of an anesthesiologist is costly. There is a general desire for systems and methods which can automatically control the administration of a hypnotic agent and an analgesic agent in a clinical anesthesia setting to thereby assist the anesthesiologist.

An automatic control system (or method) where the system input(s) depend on the system output(s) (typically via feedback) is referred to as a closed-loop control system. A closed-loop control system contrasts from an open-loop control system because an open-loop control system does not feedback system output(s) in a manner which influences the system input(s). There is a general desire for closed-loop systems and methods for automatically controlling the administration of a hypnotic agent and an analgesic agent in a clinical anesthesia setting.

Closed-loop control systems have been described to control the depth of hypnosis (DOH) of a patient by controllably administrating propofol—see Dumont G A, Martinez A, Ansermino J M. (2009). Robust Control of Depth of Anesthesia. *International Journal of Adaptive Control and Signal Processing*, 23(5): 435-454 (Dumont et al., which is hereby incorporated herein by reference); and van Heusden K, Dumont G A, Soltesz K, Petersen C L, Umedaly A, West N, Ansermino J M (2014). Design and Clinical Evaluation of Robust PID Control of Propofol Anesthesia in Children. *IEEE Transactions on Control Systems Technology*, 22(2): 491-501. DOI: 10.1109/TCST.2013.2260543 (van Heusden et al. (2014) which is hereby incorporated herein by reference). This DOH controller incorporates direct feedback from a so-called $WAV_{CNS}$ index generated by a NeuroSENSE™ monitor provided by NeuroWave Systems Inc. of Cleveland Heights, Ohio. The $WAV_{CNS}$ index generated by the NeuroSENSE™ monitor is an index which is indicative of the DOH of a patient.

Currently, there are no reliable measures indicative of a level of analgesia or nociceptive response, which can be used to provide direct feedback to a control system for the administration of analgesic. Further, it is understood that, when administered in combination, hypnotic agents and analgesic agents may interact with one another in human subjects—e.g. an analgesic agent may increase the effect (e.g. potency) of a hypnotic agent. In general, administration of an analgesic agent (in combination with a constant level of hypnotic agent) may influence the DOH of a subject and/or administration of a hypnotic agent (in combination with a constant level of analgesic) may influence a patient's nociceptive response. Further, inadequate levels of analgesia may result in sub-optimal control of hypnosis (e.g. waking up due to nociceptive stimulation). Consequently, there is a general desire for closed-loop control systems/methods for automatically controlling the administration of a combination of a hypnotic agent and an analgesic agent in a clinical anesthesia setting which incorporate feedback based on one or more indirect measures/indicia of analgesia. There is a further general desire for such control systems/methods to account for limitations of such indirect measures/indicia of analgesia The foregoing examples of the related art and limitations related thereto are intended to be illustrative and not exclusive. Other limitations of the related art will become apparent to those of skill in the art upon a reading of the description and a study of the drawings.

BRIEF DESCRIPTION OF DRAWINGS

Exemplary embodiments are illustrated in referenced figures of the drawings. It is intended that the embodiments and figures disclosed herein are to be considered illustrative rather than restrictive.

FIG. 10A shows plots of the response (versus time) of the FIG. 2 feedforward controller $F_R$ and a reference model $M_{F_R}$ on which it is based according to a particular embodiment for a step change in in $u_{R_{base}}$. FIG. 10B shows a plot (versus time) of the rate of infusion $u_R$ of analgesic agent following a step change in $u_{R_{base}}$ for the FIG. 10A feedforward controller $F_R$.

FIGS. 11A-11C (collectively, FIG. 11) show example plots (versus time) of various quantities in a combined hypnotic agent-analgesic agent control system according to a particular embodiment of the type described herein.

DESCRIPTION

Throughout the following description, specific details are set forth in order to provide a more thorough understanding to persons skilled in the art. However, well-known elements may not have been shown or described in detail to avoid unnecessarily obscuring the disclosure. Accordingly, the description and drawings are to be regarded in an illustrative, rather than a restrictive, sense.

Figure 1:
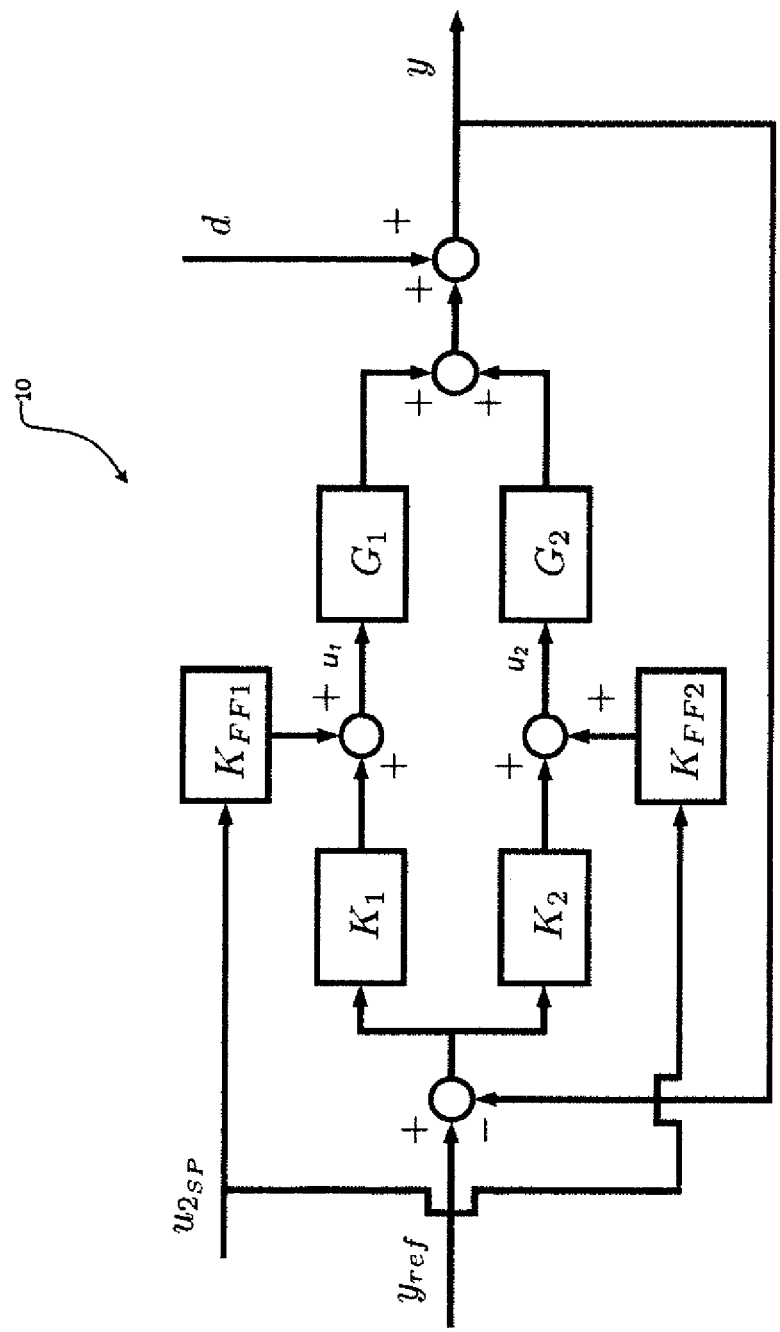
FIG. 1 schematically depicts a general habituating control system having two inputs and a single output.

FIG. 1 schematically illustrates a multi-input single-output (MISO) habituating control system 10 which may be used to describe habituating control generally. Habituating control techniques may be used in circumstances where one manipulable variable $u_1$ causes relatively rapid changes in an output variable y, although at relatively greater expense, and another manipulable variable $u_2$ causes relatively slow changes in output variable y, although at relatively low expense. Referring to FIG. 1, for control system 10, $G_1$ and $G_2$ respectively represent the given system transfer functions between the manipulable variables $u_1$ and $u_2$ and the output variable y and the output variable y is influenced by a disturbance d. The reference for the output y is provided by the input $y_{ref}$ and the set point for the variable $u_2$ is provided by the input $u_{2sp}$ that is, it is desired that y track $y_{ref}$ and $u_2$ track $u_{2sp}$. The control problem presented by the FIG. 1 control system 10 involves designing the two closed loop controllers $K_1$ and $K_2$ and the two feed-forward controllers $K_{FF1}$ and $K_{FF2}$ to achieve a set of control objectives.

In a control system 10 with two manipulated variables to, $u_2$ and one controlled output y, the control solution that satisfies steady-state requirements is not unique. To obtain a well-defined control problem, additional control objectives may be proposed which take advantage of the additional degree of freedom. By way of non-limiting example, such control objectives may include:

(i) obtaining a desired transfer function $G_y$ between $y_{ref}$ and y, where $G_y$ would be a function of the variables of the two closed loop controllers $K_1$ and $K_2$;

(ii) obtaining a desired transfer function $G_u$ between $u_{2sp}$ and $u_2$, where $G_u$ would be a function of the variables of the two closed loop controllers $K_1$ and $K_2$ and the two feed-forward controllers $K_{FF1}$ and $K_{FF2}$;

(iii) decoupling the response between $u_{2sp}$ and y;

(iv) achieve asymptotic tracking of $y_{ref}$ and $u_{2sp}$ by y and $u_2$ respectively; and (v) ensure nominal stability.

A closed loop system for the FIG. 1 system 10 which meets these objectives can be described according to the following equation:

$$\begin{bmatrix} y \\ u_1 \\ u_2 \end{bmatrix} = \begin{bmatrix} G_y & 0 & * \\ * & * & * \\ * & G_u & * \end{bmatrix} \begin{bmatrix} y_{ref} \\ u_{2_{SP}} \\ d \end{bmatrix} \quad (1)$$

This equation (1) control system can be designed to determine the desired parameters of the two closed loop controllers $K_1$ and $K_2$ and the two feed-forward controllers $K_{FF1}$ and $K_{FF2}$ which result in the desired transfer functions $G_y$ and $G_u$ of equation (1). The * in equation (1) represent transfer functions of the closed loop system that either are not under the designer's control or are not used to achieve design objectives of the control problem in this particular embodiment.

In some embodiments involving automatically controlled delivery of both hypnotic agent and analgesic agent, there is a desire to use a known closed loop DOH control system (such as, by way of non-limiting example, the system proposed by Dumont et al.) to controllably administer a hypnotic agent. Also, in some embodiments, there is a desire for the hypnotic agent control system to function where the analgesic agent is administered open loop (e.g. manually or using target controlled infusion (TCI)). In such embodiments, the FIG. 1 control system may not be directly applicable to the combined administration of hypnotic and analgesic agents, as some of the design parameters are usurped by the fixed hypnotic agent controller and are not available for the combined administration of hypnotic and analgesic agents.

Figure 2:
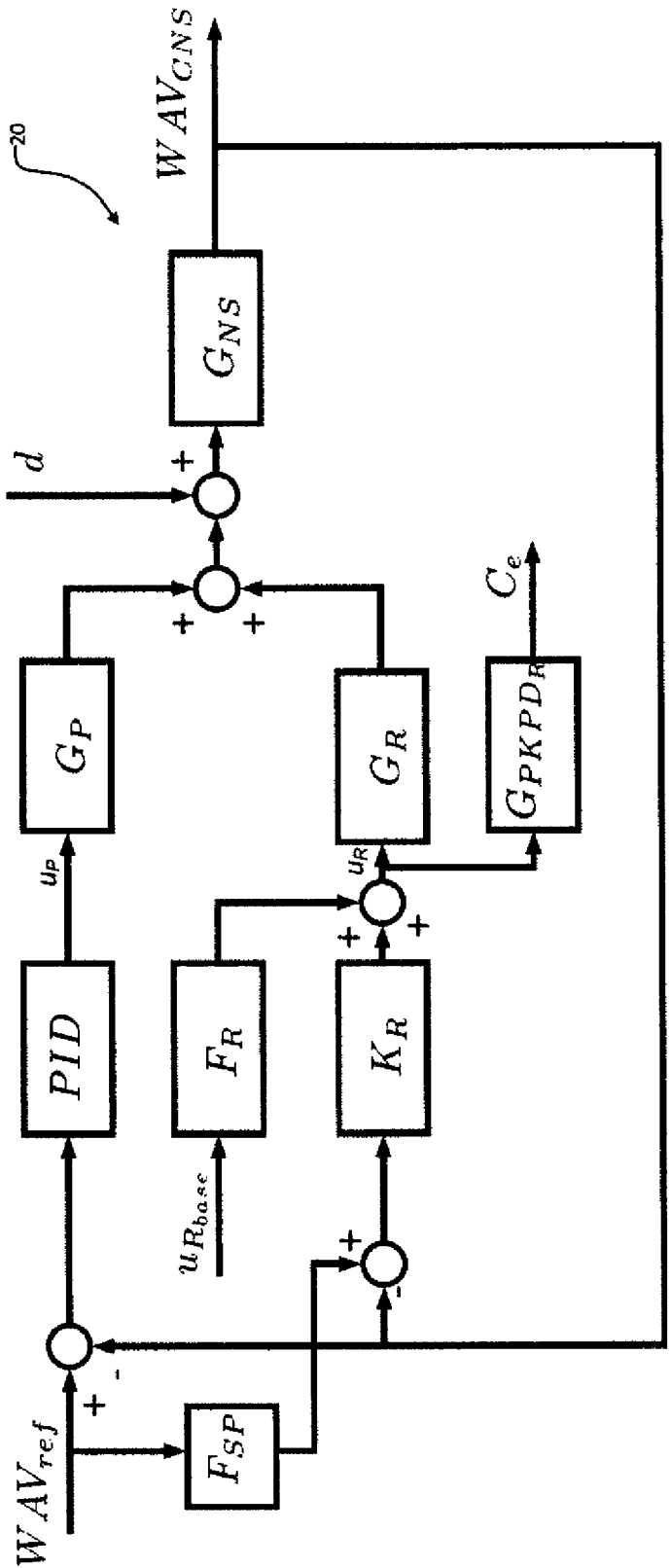
FIG. 2 schematically depicts a control system for automatically controlling the delivery of analgesic and hypnotic agents according to a particular embodiment.

In addition, in some embodiments, it may be desirable to impose different control objectives, since some information is known about the relevance of particular parameters in the context of clinical anesthesia. FIG. 2 schematically depicts a control system 20 for automatically controlled delivery of analgesic and hypnotic agents according to a particular embodiment. In the FIG. 2 control system 20: the manipulable variable $u_P$ is the infusion rate of hypnotic agent (e.g. propofol and/or the like); the manipulable variable $u_R$ is the infusion rate of analgesic (e.g. remifentanil and/or the like); the measured variable $WAV_{CNS}$ represents a DOH index; $G_P$ describes the relation between hypnotic agent infusion rate $u_P$ and $WAV_{CNS}$; $G_R$ describes the transfer function between the analgesic agent infusion rate $u_R$ and $WAV_{CNS}$; PID represents the above-described closed-loop hypnotic agent controller; $G_{NS}$ represents the dynamics of the DOH monitor; and d is representative of the disturbance caused by surgical stimulation. It will be appreciated that in practice, the transfer functions $G_P$ and $G_R$ represent characteristics of the subject/patient to whom the hypnotic agent and analgesic agent are being delivered. In some embodiments, the DOH index $WAV_{CNS}$ comprises the output by a NeuroSENSE™ DOH monitor of the type manufactured by NeuroWave Systems Inc. of Cleveland Heights, Ohio, but the measured variable $WAV_{CNS}$ may generally comprise any suitable DOH index measured by any suitable DOH monitor, such as the so-called BIS index measured by the BIS monitor (owned by Covidien, now part of Medtronic, of Minneapolis, Minn.), the index of the entropy monitor (owned by GE Healthcare of Cleveland, Ohio), the index of the SEDLine monitor (owned by Masimo of Irvine, Calif.), and/or some other DOH index or indicator which may be based on EEG data). Without loss of generality, in the embodiments described herein, the DOH index is described, without loss of generality, using the variable $WAV_{CNS}$, corresponding to the NeuroSENSE™ DOH monitor, but it will be understood that other DOH indices may be used in other embodiments.

Relatively rapid increases in the $WAV_{CNS}$ may be attributed to nociceptive response of the subject to surgical stimulation d—i.e. the surgical stimulation d causes nociceptive response in the subject and correspondingly rapid increases in the DOH index $WAV_{CNS}$. Such rapid increases in $WAV_{CNS}$ may therefore be considered to be indicative of insufficient analgesic agent. However, as discussed above, there is currently no known reliable technique for measuring the effect of analgesic agents in other circumstances (e.g. when there is little or no surgical stimulation d). In the illustrated embodiment of the FIG. 2 control system, a pharmacokinetic-pharmacodynamic model $G_{PKPD_R}$ (based on population data) is used to relate the analgesic agent infusion $u_R$ to a predicted effect site concentration $C_e$ of analgesic agent. The population-average based quantification provided by the effect site concentration $C_e$ of analgesic agent is interpretable by clinicians both in the presence of and without surgical stimulation d.

The remaining variables in the FIG. 2 control system include: $WAV_{ref}$ which represents a reference level for the measured DOH index $WAV_{CNS}$; $u_{R_{base}}$ which represents a baseline level for the infusion rate of the analgesic agent; $K_R$ which represents the closed loop analgesic agent controller; and $F_R$ and $F_{SP}$ which represent feedforward filters. In some embodiments, the baseline level for the analgesic agent infusion rate $u_{R_{base}}$ may be a user-specified input (e.g. specified by an anesthesiologist), although this is not necessary and, in some embodiments, the baseline level for the analgesic agent infusion rate $u_{R_{base}}$ may be automatically determined by a suitable controller (not shown). In some embodiments, the baseline level for the analgesic agent infusion rate $u_{R_{base}}$ may be based on measurement of an independent nociception index (e.g. the analgesic/nociception index (ANI)). For the purposes of this description, it is assumed, without loss of generality, that the baseline level for the analgesic agent infusion rate $u_{R_{base}}$ is a system input.

It will be appreciated based on the discussion above that the closed loop controller $K_R$ and the feedforward filters $F_R$ and $F_{SP}$ are not fixed and may be designed satisfy a number of control objectives. In particular, the FIG. 2 control system can be described according to:

$$\begin{bmatrix} WAV_{CNS} \\ C_e \end{bmatrix} = \begin{bmatrix} T & * & * \\ * & M_{FF} & M_d \end{bmatrix} \begin{bmatrix} WAV_{ref} \\ U_{R_{base}} \\ d \end{bmatrix} \quad (2)$$

where: T is the transfer function between $WAV_{ref}$ and $WAV_{CNS}$, $M_d$ is a desired transfer function between d and $C_e$ (also referred to herein as the objective function $M_d$ or the objective $M_d$); and $M_{FF}$ is a desired relationship between $u_{R_{base}}$ and $C_e$. The relationship between $WAV_{ref}$ and $C_e$ can be shaped by the feedforward filter $F_{SP}$. Since, in the case of the illustrated embodiment, the PID controller is fixed, T and $M_d$ are not generally independent.

In some embodiments, control system 20 is designed to satisfy robust stability requirements. In such embodiments, it may be desirable to ascertain nominal model(s) and uncertainties for the effect of the hypnotic agent and the analgesic agent. Since control system 20 of the FIG. 2 embodiment is designed as an addition to the existing closed loop PID controller for the administration of hypnotic agent, models identified from closed-loop data incorporating this PID hypnotic agent controller may be used to determine the nominal model for the effect of the hypnotic agent. For the case of the analgesic agent, the nominal model may be based on pharmacokinetic-pharmacodynamic (PKPD) models.

For the case of the hypnotic agent, data from clinical evaluation of the closed-loop PID propofol control system described by Dumont et al. were available for model identification. PKPD models for this closed-loop PID propofol control system have been identified in accordance with the approach described in K. van Heusden, J. Ansermino, K. Soltesz, S. Khosravi, N. West, and G. Dumont, "Quantification of the variability in response to propofol administration in children," *Biomedical Engineering, IEEE Transactions on*, vol. 60, no. 9, pp. 2521-2529, 2013 (Van Heusden et al. (2013), which is hereby incorporated herein by reference. The resulting set of models adequately describes the interpatient variability observed in the study population and is validated for the design of a robust linear controller, provided the implementation conditions are similar to the conditions during data collection. In some embodiments of the FIG. 2 control system, the analgesic agent controller functions as an addition to the existing closed-loop PID hypnotic agent control system described by Dumont et al. and the implementation conditions for the hypnotic agent may be similar to the conditions under which the Van Heusden et al. (2013) models were developed.

A nominal hypnotic agent model $G_{0_P}$, and model uncertainty $w_{I_P}$ based on this model set is not unique. Since the Dumont et al. PID hypnotic agent controller is known to robustly stabilize the closed-loop hypnotic agent control system, and, in the FIG. 2 embodiment, the analgesic controller is added to the Dumont et al. PID hypnotic agent control system, a minimal requirement for the nominal hypnotic agent model and uncertainty is that they satisfy the robust stability criterion $\|Tw_{IP}\|_\infty < 1$, where T is the complementary sensitivity of the nominal hypnotic agent model $G_{0_P}$ when controlled by the Dumont et al. PID controller, and $w_{IP}$ describes the model uncertainty. To achieve this requirement, a nominal hypnotic agent model $G_{0_P}$ may be identified by minimizing the 2-norm of the worst case error of the complementary sensitivity T according to:

$$G_{0_P} = \underset{G}{\operatorname{argmin}} \sum_{\omega \in \Omega} \max_{M_i, i \in [1,N]} \quad (3)$$

$$\left| \frac{PID(j\omega)M_i(j\omega)}{1 + PID(j\omega)M_i(j\omega)} - \frac{PID(j\omega)G(j\omega)}{1 + PID(j\omega)G(j\omega)} \right|$$

where: $M_i$, $i \in [1,N]$ denotes a set of N models M; $G_{0_P}$ is the nominal model relating the effect of the hypnotic agent infusion ($u_P$) to $WAV_{CNS}$; and PID describes the Dumont et al. hypnotic agent controller. In one particular embodiment, $\Omega$ is set of 1000 logarithmically spaced frequencies between 0.0001 and 0.1 rad/s, although it will be appreciated that nominal models may be developed using different frequency sets. The hypnotic agent model uncertainty may then be defined as:

$$W_{I_P}(j\omega) = \max_{M_i, i \in [1,N]} \left| \frac{M_i(j\omega) - G_{0_P}(j\omega)}{G_{0_P}(j\omega)} \right| \qquad (4)$$

Choosing a nominal model $G_{0_P}$ according to this approach may ensure that the nominal model $G_{0_P}$ and the resulting model uncertainty satisfy the robust stability criterion $\|Tw_{I_P}\|_\infty < 1$.

Figure 3:
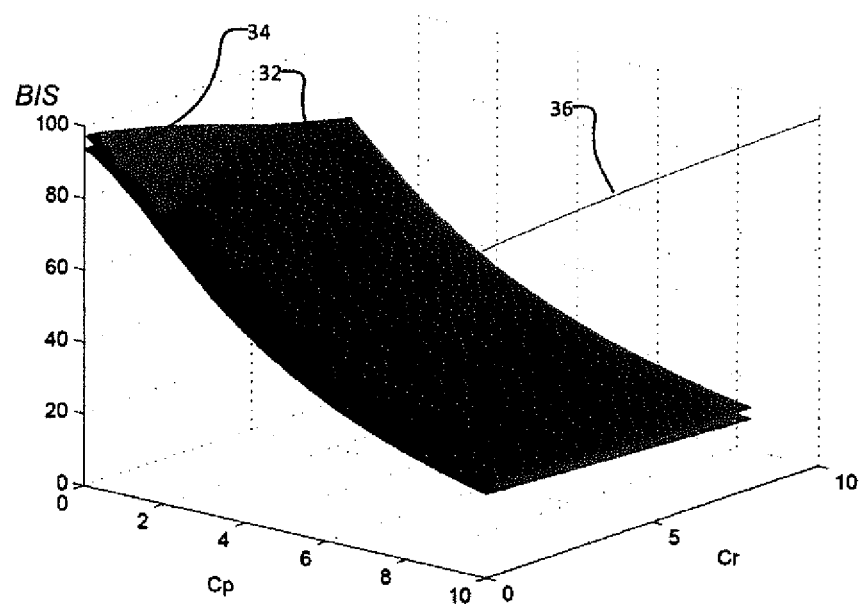
FIG. 3 shows the results of a number of studies illustrating the effect of the combination of propofol and remifentanil on the BIS indicator of DOH.

Turning now to modelling the effect of analgesic agent infusion rate on DOH, published results tend to be contradictory and to depend on the experimental setting and the presence of stimulation. A number of studies have been performed using the so-called BIS parameter as the indicator of DOH. FIG. 3 shows the results of studies conducted on children (as published by C. Jeleazcov, H. Ihmsen, J. Schmidt, C. Ammon, H. Schwilden, J. Schüttler, and J. Fechner, "Pharmacodynamic modelling of the bispectral index response to propofol-based anaesthesia during general surgery in children," *British Journal of Anaesthesia*, vol. 100, no. 4, pp. 509-516, 2008) and adults (as published by T. W. Bouillon, J. Bruhn, L. Radulescu, C. Andresen, T. J. Shafer, C. Cohane, and S. L. Shafer, "Pharmacodynamic interaction between propofol and remifentanil regarding hypnosis, tolerance of laryngoscopy, bispectral index, and electroencephalographic approximate entropy." *Anesthesiology*, vol. 100, no. 6, pp. 1353-72, June 2004 (Bouillon et al., which is hereby incorporated herein by reference). The results of these studies are shown in FIG. 3 as the differently shaded surfaces 32 and 34 and exhibit similar results in the absence of stimulation, where the vertical axis is BIS index and the horizontal axes Cp and Cr are respectively effect site concentrations of propofol and remifentanil. Propofol and remifentanil combinations that maintain the BIS index between 45 and 55 in the presence of stimulation are reported in H. Röpcke, M. Könen-Bergmann, M. Cuhls, T. Bouillon, and A. Hoeft,"Propofol and remifentanil pharmacodynamic interaction during orthopedic surgical procedures as measured by effects on bispectral index," *Journal of Clinical Anesthesia*, vol. 13, no. 3, pp. 198-207, 2001. Although the reported drug requirements during stimulation were higher than the reported values without stimulation, the shape of the curve (which is shown in FIG. 3 as the blue line 36) remained similar. In particular, at higher levels of remifentanil, the shape of the curve 36 (with stimulation) follows surfaces 32, 34 (without stimulation) quite nicely, but with higher levels of propofol. For lower levels of remifentanil, significantly higher levels of propofol may be desired. In this way, FIG. 3 exhibits a difference between a situation with stimulation and without. These response surface models 32, 34, 36 confirm that the effect of remifentanil is higher at BIS levels corresponding to sedation (e.g. approximately above BIS=70) than at levels for general anesthesia (e.g. approximately between 40<BIS<60).

From the Bouillon et al. adult interaction data, a worst case linear gain can be determined for the effect of remifentanil on DOH. In some embodiment, the remifentanil model combines a population-based remifentanil pharmacokinetic-pharmacodymanic (PKPD) model (e.g. the model described by C. Minto, T. Schnider, T. Egan, E. Youngs, H. Lemmens, P. Gambus, V. Billard, J. Hoke, K. Moore, D. Hermann, K. Muir, J. Mandema, and S. Shafer, "Influence of age and gender on the pharmacokinetics and pharmacodynamics of remifentanil. i. model development." *Anesthesiology*, vol. 86, no. 1, pp. 10-23, 1997 (Minto et al., which is hereby incorporated herein by reference) with the linearized gain based on an interaction model, such as, by way of non-limiting example, the interaction model described by Bouillon et al. The model is given by:

$$BIS = E0\left(1 - \frac{(C_{e_R}/C_{r_{50}} + C_{e_P}/C_{p_{50}})^\gamma}{1 + (C_{e_R}/C_{r_{50}} + C_{e_P}/C_{p_{50}})^\gamma}\right) \qquad (5)$$

where $E_0=97.4$, $C_{r_{50}}=19.3$, $C_{p_{50}}=4.47$ and $\gamma=1.43$. The derivative $$\frac{dBIS}{dC_{e_R}}$$

can be calculated and is given by:

$$dBIS/dC_{e_R} = \frac{E_0\gamma}{C_{r_{50}}} \frac{(C_{e_R}/C_{r_{50}} + C_{e_P}/C_{p_{50}})^{\gamma-1}}{(1 + (C_{e_R}/C_{r_{50}} + C_{e_P}/C_{p_{50}})^\gamma)^2} \qquad (6)$$

Equations (5) and (6) show that over the range of interest (e.g. $C_{e_R} \in [0,12]$, $C_{e_P} \in [0,10]$, the maximal derivative is bounded by $$\frac{dBIS}{dC_{e_R}} \leq 3.1 = G_{R_{max}}.$$

Accordingly, the maximal effect of the analgesic agent on $WAV_{CNS}$ may then be described as:

$$G_R = G_{PKPD_R} G_{R_{max}} \qquad (7)$$

where: $G_R$ is the worst case model of the effect of the analgesic agent on $WAV_{CNS}$ (see FIG. 2); $G_{PKPD_R}$ is a suitable model of the relationship between the rate of analgesic agent infusion $u_R$ and the predicted effect site concentration $C_e$ (see below); and $G_{R_{max}}$ is the maximum slope of $$\frac{dBIS}{dC_{e_R}}$$

in the range of interest. Since the equation (7) worst case gain is achieved for relatively high BIS values, corresponding to sedation and not general anesthesia, it follows that during maintenance of anesthesia (e.g. at BIS levels in a range of 40-60), the effect of analgesic agent (e.g. remifentanil) on the DOH is negligible compared to the effect of hypnotic agent (e.g. propofol). However, for the purpose of robustness analysis and stability analysis in the presence of nonlinearities, this worst-case gain can be taken into account. Accordingly, when designing a controller, different models may be used for the different objectives and constraints.

In some embodiments, for the purposes of implementing a model-matching controller for the FIG. 2 system 20 and for modelling the effect of analgesic agent, the effect of the analgesic agent infusion rate $u_R$ on the $WAV_{CNS}$ may be assumed to be negligible for the model-matching controller design of FIG. 2 and defined in equation (2)—i.e. $G_R=0$ (see FIG. 2). In some embodiments, the relation $G_{PKPD_R}$ between the rate of analgesic agent infusion $u_R$ and the predicted effect site concentration $C_e$ may be described by a pharmacokinetic-pharmacodynamic (PKPD) model. In one particular embodiment, where the analgesic agent is remifentanil, this relation $G_{PKPD_R}$ may be provided by the model described by Minto et al., as discussed above.

For the purposes of designing a robust controller and performing robustness analysis, however, it may be undesirable, in some embodiments, to assume that the effect of analgesic agent infusion rate $u_R$ on the $WAV_{CNS}$ is negligible. Instead, in some such embodiments, the worst cast gain $G_{R_{max}}$ reported in the literature (or some other suitable selected worst case gain) may be used in combination with the Minto et al. pharmacokinetic-pharmacodynamic model according to equation (7). In some embodiments which use the Minto et al. model, the Minto et al. models $M_{R_i}$ may be defined for an appropriate population. A nominal model may be defined by minimizing the 2-norm of the modelling error according to:

$$G_{0_R} = \underset{G_R}{\text{argmin}} \sum_{\omega \in \Omega} \underset{M_{R_i}, i \in [1,N]}{\max} |M_{R_i}(j\omega) - G_R(j\omega)| \quad (7A)$$

where $G_{0_R}$ is the nominal model. The multiplicative uncertainty $w_{I_R}$ may then be defined accordingly as:

$$w_{I_R}(j\omega) = \underset{M_{R_i}, i \in [1,N]}{\max} \left| \frac{M_{R_i}(j\omega) - G_{0_R}(j\omega)}{G_{0_R}(j\omega)} \right| \quad (7B)$$

In some embodiments, the equation (7A) nominal model of the effect of analgesic agent infusion rate $u_R$ on the $WAV_{CNS}$ together with the worst case gain $G_{R_{max}}$ may be used to design for stability in the presence of non-linearities.

In some embodiments, the FIG. 2 control system 20 may be designed to achieve a number of design objectives, which can be translated into control objectives.

One design objective involves the desirability of increasing the rate of infusion of analgesic agent in response to nociceptive stimulation. This design objective is motivated by the observation that relatively rapid changes (increases) in the DOH are often caused by nociception. However, measures of DOH (like $WAV_{CNS}$ discussed above) are not direct measures of analgesia. Currently available models which relate DOH to infusion rates of analgesic agents focus on the achieved DOH in the absence of nociceptive stimulation and do not account for the level of analgesic agent desirable to suppress nociception. Further, different combinations of analgesic agent and hypnotic agent may lead to the same level of DOH, but may also lead to significantly different levels of response to stimulation. Accordingly, in some embodiments, an indirect control objective may be used to shaped the rate of infusion of analgesic agent $u_R$ to disturbances d (i.e. nociceptive stimulation).

In some embodiments, the design objectives are based on a number of assumptions. In some embodiments, it is assumed that the hypnotic agent controller (e.g. the PID controller shown in the FIG. 2 system 20) adequately controls the DOH of the subject. This assumption is motivated by clinical evaluation of the Dumont et al. PID propofol controller. In some embodiments, it may also be assumed that, in the absence of surgical stimulation, the noise affecting the measured DOH level (e.g. $WAV_{CNS}$ in the FIG. 2 system) is zero mean.

In some embodiments, a first design objective involves increasing the infusion rate for analgesic agent when it is detected that a subject has responded to surgical stimulation. As mentioned above, relatively rapid increases in DOH level (e.g. $WAV_{CNS}$) may be indicative of response to stimulation. In terms of the FIG. 2 control system 20, nociceptive stimulation is represented by the disturbance d(t). A design objective may therefore be to respond to rapid increases in disturbance d(t) with a clinically relevant increase in the rate of infusion of analgesic agent $u_R(t)$. In some embodiments, this increase in the rate of infusion of analgesic agent $u_R(t)$ may be parameterized by a corresponding increase in the effect site concentration $C_e$. In some embodiments, the design objective between a rapid increase in $WAV_{CNS}$ (DOH level) and effect site concentration $C_e$ may involve a rapid increase in effect site concentration $C_e$ by an amount that is proportional to the increase in $WAV_{CNS}$ (DOH level) (e.g. for a DOH level increase of x, there is a desire for the effect site concentration $C_e$ to rapidly increase by an amount y, where y is proportional to x). In one particular embodiment, this design objective is set such that for an increased in $WAV_{CNS}$ index of 10, there is a desire to rapidly increase the rate of infusion of analgesic agent $u_R$ by an amount which corresponds to a predicted effect site concentration $C_e$ of 2 ng/ml. As described above in connection with the development of equation (2), the transfer function between the effect site concentration $C_e(t)$ of analgesic agent and nociceptive stimulation d(t) may be designed to match an objective function $M_d(s)$ as shown in equation (8) below.

$$C_e(s) = \frac{G_{PKPD_R} K_R G_{NS}}{1 + G_{NS}(PIDG_P + K_R G_R)} d(s) = M_d(s)d(s) \quad (8)$$

Accordingly, the objective function $M_d(s)$ may be designed to meet one or more of the design objectives described herein and a controller may be designed to match the objective function $M_d(s)$. By way of non-limiting example, the objective function $M_d(s)$ may be designed such that for a measured step disturbance d of 10 in $WAV_{CNS}$, the predicted effect site concentration $C_e$ of analgesic agent rapidly increases by 2 ng/ml in accordance with the particular design objective described above. It will be appreciated that, in other embodiments, objective function $M_d(s)$ may be designed to meet other design objective(s) as between the rate of infusion of analgesic agent $u_R$ (and/or the corresponding effect site concentration $C_e(t)$ of analgesic agent) and a nociceptive disturbance d (and/or the corresponding $WAV_{CNS}$ response to stimulation).

As discussed above, for the purposes of model-matching, some embodiments involve assuming that $G_R=0$ (i.e. the effect of analgesic agent infusion rate on DOH is negligible), in which case equation (8) reduces to:

$$M_d = \frac{G_{PKPD_R} K_R G_{NS}}{1 + G_{NS} PIDG_P} \quad (9)$$

which leads to $$K_R = \frac{M_d}{G_{PKPD_R}} \frac{1 + G_{NS} PIDG_P}{G_{NS}} = \frac{M_d}{G_{PKPD_R} S_P} \quad (10)$$

where $S_P$ is the sensitivity function of the hypnotic agent loop.

In some embodiments, another design objective involves avoiding extended periods of low or zero analgesic agent infusion. Extended periods of low or zero analgesic agent infusion could lead to insufficient analgesia and may be clinically undesirable, even in the absence of any response (as measured by DOH level—e.g. $WAV_{CNS}$) to stimulation d. In some embodiments, a lower bound or baseline may be provided for the rate of infusion of analgesic agent $u_R$. Such lower bound or baseline may be constant (although this is not necessary) and may be user- (e.g. anesthesiologist-) configurable.

In some embodiments, another design objective may involve permitting a user (e.g. an anesthesiologist) to control the rate of analgesic agent infusion $u_R$ in the absence of stimulation d. This objective may minimize the likelihood that the analgesic infusion rate $u_R$ is undesirably impacted by steady-state and/or low-frequency errors in the controller DOH level (e.g. $WAV_{CNS}$) to and/or measurement noise. In some embodiments, the user control of the rate of analgesic agent infusion $u_R$ may involve causing the rate of analgesic agent infusion $u_R$ to return to the baseline or lower bound level, although this is not necessary. In embodiments where providing user-control of rate of analgesic agent infusion $u_R$ involves causing the rate of analgesic agent infusion $u_R$ to return to a constant baseline level or lower bound in the presence of low frequency or steady state error between the measured DOH level (e.g. $WAV_{CNS}$) and the desired DOH level (e.g. $WAV_{ref}$), this design objective may be implemented as a control objective by designing the analgesic agent controller $K_R$ to have a zero at s=0—i.e. $K_R(0)=0$.

In the absence of stimulation, the measured DOH level (e.g. $WAV_{CNS}$) is affected by noise. Due to the closed-loop analgesic agent controller $K_R$, this noise will affect the rate of infusion of the analgesic agent $u_R$. Since the noise is assumed to be zero mean, this will not affect the average level of analgesia. However, where there is a lower bound on the rate of analgesic agent infusion $u_R$, the effect of zero mean noise on the average analgesic agent infusion rate will not be zero mean. Consequently, in some embodiments, the effect of measurement noise on the average analgesic agent infusion rate may be bounded to maintain user control of the baseline rate of analgesic agent infusion. It may be shown that bounding the effect of measurement noise on the average analgesic agent infusion rate, for sinusoidal disturbances, may correspond to a constraint on the worst case gain for $K_R$ given by the infinity-norm $\|K_R\|_\infty$. This constraint on $\|K_R\|_\infty$ may in turn correspond to a constraint on the achievable (desired) transfer function $M_d$ (see equation (2)).

The amplification of noise to the analgesic agent input signal $u_R$ is determined by:

$$u_R = \frac{K_R G_{NS}}{1+G_{NS}(PIDG_P+K_RG_R)}d(s) = K_R Sd(s) \quad (11)$$

where S is the sensitivity function of the loop containing $G_R$ and $G_P$.

Assuming that the disturbance d is a sinusoid with frequency ω, i.e. $d(t)=\sin(\omega t)$ and defining $d_S(s)=S(s)d(s)$, it follows that $d_S(t)$ is a sinusoidal noise signal. The worst case amplitude of $d_S(t)$ was estimated from clinical evaluation of the PID hypnotic agent closed-loop system, and determined to be limited to 7 $WAV_{CNS}$ units. Accordingly, in some embodiments, it is therefore assumed that $\max_\omega(\sup_t|d_S(\omega t)|)<7$. The effect of this noise on the analgesic agent input signal $u_R$ is then a sinusoid $u_R(t)$, with the worst case amplitude $\|u_R\|_\infty=\max_\omega(\sup_t|u_R(\omega t)|)$ limited by:

$$\|u_R\|_\infty \leq \|K_R\|_\infty \max_\omega(\sup_t|d_S(\omega t)|) = 7\|K_R\|_\infty \quad (12)$$

Figure 4:
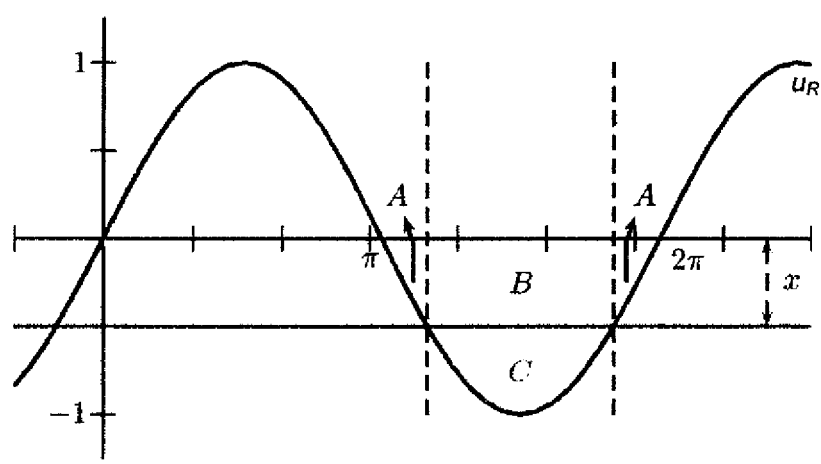
FIG. 4 is a plot showing the effect of sinusoidal noise on a constrained infusion rate of analgesic agent.

The average increase in analgesic agent infusion rate due to saturation depends on the amplitude of the zero mean noise. Consider the (constrained) sinusoidal signal shown in FIG. 4. If there is no constraint on the analgesic agent infusion rate $u_R$, the average of the analgesic infusion rate is the integral of the sinusoid, from 0 to 2π, which equals 0. However, if there is a constraint (e.g. baseline 40) on the analgesic agent infusion rate $u_R$, the average infusion rate is increased by C/(2π), where C=2−2A−B and $$A=\int_0^{\arcsin(x)}\sin z\, dz=$$

$$-\cos(\arcsin(x))+\cos(0)=(1-\sqrt{1-x^2})$$

$$B=x(\pi-2\arcsin(x)) \quad (13)$$

where x is the baseline rate of analgesic agent infusion. It follows that the increase in the average analgesic agent infusion rate is given by:

$$\Delta u_{mean} = \frac{C}{2\pi} = \frac{2-x(\pi-2\arcsin(x))-2\left(1-\sqrt{1-x^2}\right)}{2\pi} \quad (14)$$

For a sine wave with amplitude $\|u_R\|_\infty$, and a base infusion rate of $u_{R_{base}}$, this scales to:

$$\Delta u_{mean} = \|u_R\|_\infty \left(\frac{2}{2\pi} - \frac{\left(\frac{u_{R_{base}}}{\|u_R\|_\infty}\right)\left(\pi-2\arcsin\left(\frac{u_{R_{base}}}{\|u_R\|_\infty}\right)\right) - 2\left(1-\sqrt{1-\left(\frac{u_{R_{base}}}{\|u_R\|_\infty}\right)^2}\right)}{2\pi}\right) \quad (15)$$

If it is assumed that the baseline analgesic agent infusion rate is denoted $u_{R_{base}}$ which corresponds to a predicted baseline effect site concentration of $C_{eR_{base}}$, some embodiments may comprise defining a maximal allowed change in the baseline predicted effect site concentration to be $\Delta C_e$. The corresponding bound on $\Delta u_{mean}$ may be defined as:

$$\Delta u_{mean} < K_{max} < u_{R_{base}}\frac{\Delta C_e}{C_{eR_{base}}} \quad (15A)$$

Where $K_{max}$ is defined (by equation (15A)) as the upper bound on $\Delta u_{mean}$.

Equations (15) and (15A) may be used to define an upper bound on $\|K_R\|_\infty$. Noting that $$K_R = \frac{M_d}{S_P G_{PKPD_R}},$$

requiring $7\|K_R\|_\infty < K_{max}$ is equivalent to requiring $$\left\|\frac{M_d}{S_P G_{PKPD_R}}\right\|_\infty < \frac{K_{max}}{7}.$$

It follows that:

$$|M_d(\omega)| < \frac{|S_P(\omega)G_{PKPD_R}(\omega)|K_{max}}{7}, \forall \omega \quad (16)$$

which imposes a bound on the on the desired transfer function $M_d$ between d and $C_e$ (see equation (2)).

In some embodiments, yet another design objective involves providing so-called robust stability, in particular with respect to inter-patient variability and non-linear interaction between the hypnotic agent (e.g. propofol) and the analgesic agent (e.g. remifentanil). Even though the Dumont et al. PID controller is known to robustly control the infusion rate of hypnotic agent at constant levels of analgesic agent, it is desirable to design a control system for the combination of hypnotic and analgesic agents that is robustly stable, particularly when the infusion rates of analgesic are controlled using the same error signal as the hypnotic agent loop. This design objective may be used to provide one or more additional control objectives. In some embodiments, this design objective is used to provide two or more additional control objectives.

Robustness of MISO systems including mid-ranging schemes has been evaluated by W. P. Heath and S. Gayadeen, "Simple robustness measures for control of miso and simo plants," Proc. 18th IFAC World Congr, pp. 11 356-11 361, 2011 (Heath et al., which is hereby incorporated herein by reference). The results are obtained from a straightforward application robust control theory, using the fact that the loop function is a simple addition of the different loops. For the case of the FIG. 2 system 20 and its combined hypnotic agent-analgesic agent control system, the loop function may be given by $L = G_{NS}(PIDG_P + K_R G_R)$. If the MISO system is defined according to $y = \sum_{i=1}^{n} G_i(1+\omega_i \Delta_i)u_i$, where the uncertainties $\Delta_i$ are assumed to be linear time-invariant (LTI) and satisfy $\|\Delta_i\|_\infty \leq 1$, the system will be robustly stable if $$\sum_{i=1}^{n} |G_i(j\omega)C_i(j\omega)\omega_i(j\omega)| \leq |1 + \sum_{i=1}^{n} G_i(j\omega)C_i(j\omega)| \quad (16A)$$

Application of equation (16A) to the FIG. 2 analgesic agent-hypnotic agent control system 20 yields the following constraint:

$$|G_{NS}G_{O_P}(j\omega)PID(j\omega)\omega_{I_P}(j\omega)| + |G_{NS}G_{O_R}(j\omega)K_R(j\omega)\omega_{I_R}(j\omega)|$$

$$\leq |1 + G_{NS}G_{O_P}(j\omega)PID(j\omega) + G_{NS}G_{O_R}(j\omega)K_R(j\omega)| \quad (17)$$

In some embodiments, the small gain theorem may be applied to lead to an additional constraint that guarantees stability in the presence of nonlinearities. Consider the block diagram shown in FIG. 5. In the FIG. 5 schematic illustration, nonlinear behavior due to interaction between drugs or nonlinear characteristics, are taken into account in the nonlinear response to analgesic agent infusion. As discussed above, the Dumont et al. hypnotic agent closed-loop system is known to be robustly stable and the loop function is given by $$S_P = \frac{G_{NS}}{1 + G_{NS}G_P PID} \quad (17A)$$

Figure 5:
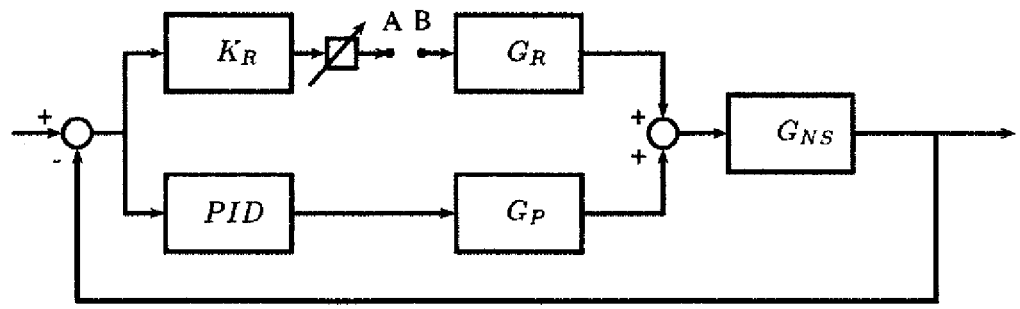
FIG. 5 is a schematic block diagram of the FIG. 2 closed loop system for controlled delivery of analgesic and hypnotic agents showing the portions of the system that are used for stability analysis.

Using the small gain theorem, the closed-loop system of FIG. 5 including the analgesic agent loop is stable if the gain of the loop from B to A is smaller than 1:

$$\left\| \frac{K_R G_{NS} G_R}{1 + G_{NS} G_P PID} \right\|_\infty \gamma < 1 \quad (18)$$

$$\|K_R G_R S_P\|_\infty \gamma < 1$$

where $\gamma$ is the maximal gain of the non-linearity. Without loss of generality, we may define $\gamma \leq 1$ and $G_R = G_{PKPD_R} G_{R_{max}}$, where $G_{R_{max}}$ is the worst case linearized gain of the hypnotic agent-analgesic agent interaction surface (see FIG. 3) to changes in analgesic concentration at constant hypnotic agent concentrations. It follows that the equation (18) condition reduces to $\|K_R G_{PKPD_R} G_{R_{max}} S_P\|_\infty < 1$. Note that $K_R S_P G_{PKPD_R} = M_d$ and the robust stability condition further reduces to $$\|M_d\|_\infty G_{R_{max}} < 1 \quad (19)$$

With the above-discussed design objectives and control objectives, a suitable controller design according to a particular embodiment is now described in terms of the desired transfer function (objective) $M_d$ which describes the relationship between the disturbance d and the effect site analgesic concentration $C_e$ (see equation (2))—i.e. a technique is described for designing a controller to match the objective function $M_d$ according to a particular embodiment. The control objectives impose constraints on the desired transfer function $M_d$ and may be summarized as follows: (1) the objective function $M_d(s)$ should achieve a predicted effect site analgesic agent concentration $C_e$ in response to a disturbance d in the DOH (e.g. a step disturbance d in $WAV_{CNS}$ which may be attributed to a nociceptive response). As discussed above, in one particular embodiment, the objective function $M_d(s)$ may be designed such that the response to a step disturbance d of 10 units of $WAV_{CNS}$ corresponds to an increase in predicted effect site concentration $C_e$ of analgesic agent of 2 ng/ml. (2) $K_R(0)=0$ to ensure that the rate of analgesic infusion $u_R$ returns to the user-configurable baseline in the absence of stimulation. (3) $|M_d(j\omega)| <$ $$|M_d(j\omega)| < \frac{|S_P(j\omega)G_{PKPD_R}(j\omega)|K_{max}}{7}, \quad (3)$$

$\forall \omega$ which corresponds to the equation (16) criterion for the particular embodiment where the worst case amplitude of Sd(s) is set to be 7 $WAV_{CNS}$ units (it being understood that other criteria may be used for other worst case Sd(s) amplitudes). (4) $\|M_d\|_\infty G_{R_{max}} < 1$ which corresponds to the equation (19) small-gain stability criterion. It is noted that these design objectives and control objectives are exemplary design and control objectives that are used to design a controller in accordance with one particular embodiment. In other embodiments, other control and/or design objectives could be used. By way of non-limiting example, any of the numerical constants used in these control and/or design objectives and/or constraints described herein could be replaced by any other suitable numerical constants.

In some embodiments, the analgesic agent controller described below (in addition to the closed loop PID hypnotic agent controller) may be allometrically scaled. In one particular embodiment, the analgesic controller may be scaled using an allometric scaling factor $$C_{allom} = \left(\frac{bwt}{70}\right)^{0.75}$$

where bwt represents body weight.

From equation (10) above, $$M_d = K_R G_{PKPD_R} S_P \quad (19A)$$

where $$S_P = \frac{G_{NS}}{1 + G_{NS} G_P PID}.$$

It is known that the Dumont et al. PID hypnotic agent controller includes an integrator, and, consequently, $S_P(0) = 0$. The Minto et al. pharmacokinetic-pharmacodynamic model $G_{PKPD_R}$ does not include an integrator, nor does it include any zeros at s=0. Accordingly, to achieve control objective (2) above (i.e. $K_R(0)=0$), the desired transfer function $M_d$ may be designed to have two zeros at s=0. This implies that in such embodiments, the step response of the desired transfer function $M_d$ will have an undershoot.

In some embodiments, the maximal allowed change to the baseline predicted effect site concentration of analgesic agent $\Delta C_e$ may be a set to be a constant. In some embodiments, this parameter $\Delta C_e$ may be user-configurable. In one particular embodiment, the maximal allowed change to the baseline predicted effect site concentration of analgesic agent $\Delta C_e$ is set to be $\Delta C_e$ 4.5. The selection of the parameter $\Delta C_e$ may be used to define $K_{max}$ according to equation (15A), which may in turn be used to constrain $|M_d(\omega)|$ according to equation (16) and control objective (3) described above.

In one particular embodiment, the inventors have selected an objective (i.e. an $M_d(s)$) to meet the control/design objectives and constraints according to:

$$M_d(s) = 0.75 G_{NS} \frac{300s}{300s+1} \frac{90s}{90s+1} \frac{1}{60s+1} \frac{1}{80s+1} \quad (20)$$

Figure 6:
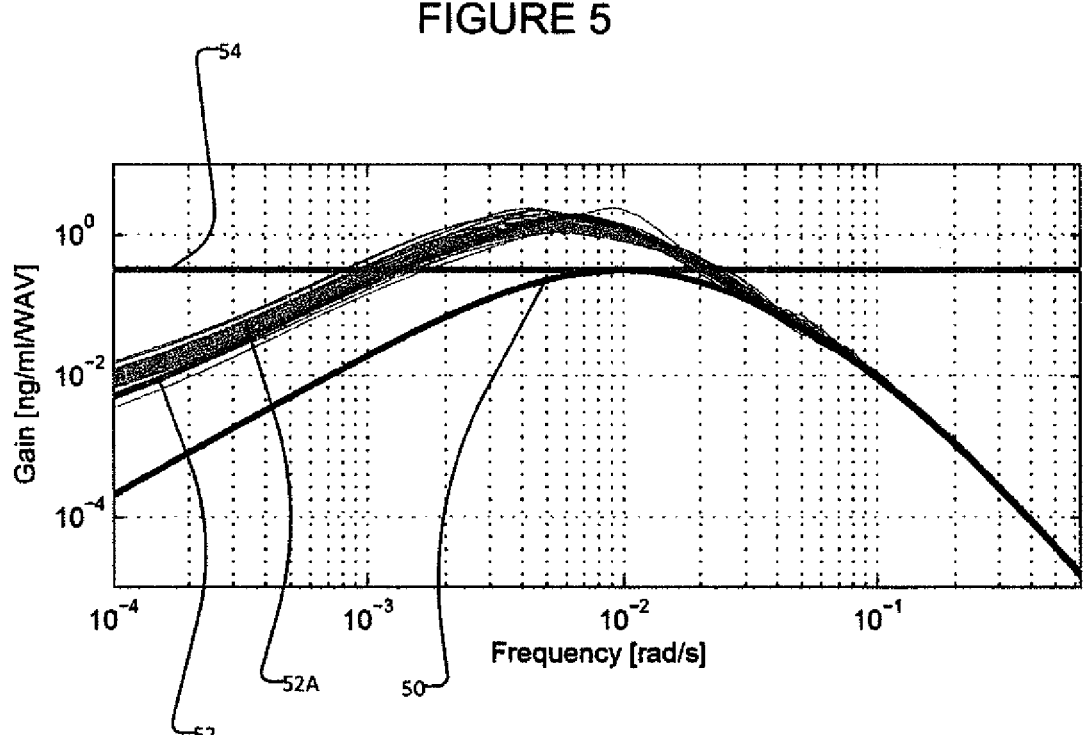
FIG. 6 shows the Bode magnitude frequency response of a desired transfer function $M_d$ between a surgical stimulation d and an effect site concentration $C_e$ of analgesic agent according to a particular embodiment together with a number of the controller design constraints used in accordance with a particular embodiment.
Figure 7A:
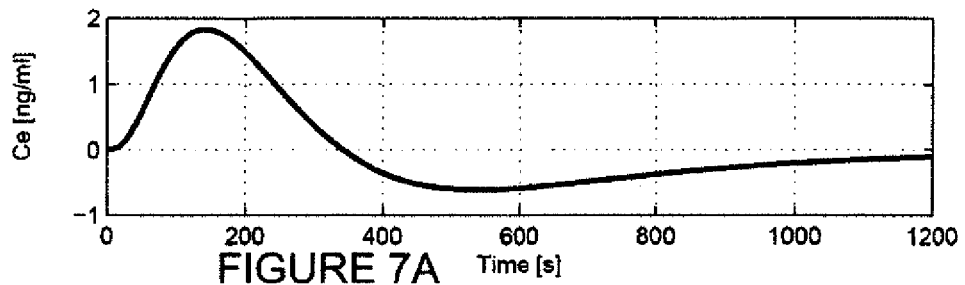
FIGS. 7A and 7B (collectively, FIG. 7) respectively show the response of the predicted effect site concentration of analgesic agent and analgesic infusion rate in response to a step disturbance of 10 units of $WAV_{CNS}$ in a desired response according to a particular embodiment.
Figure 7B:
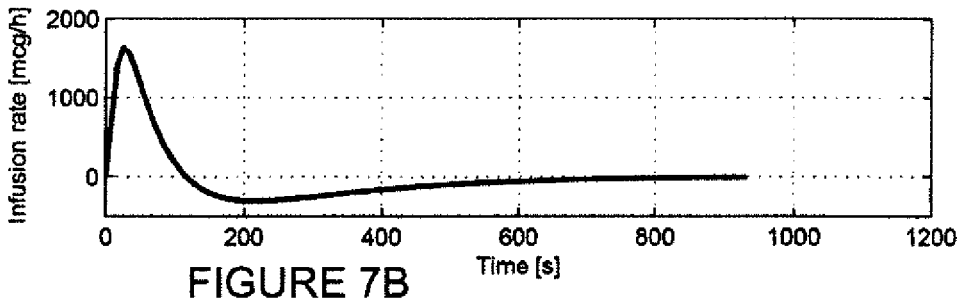

FIG. 6 shows the Bode magnitude frequency response of the equation (20) objective function $M_d$ 50, together with the equation (16)/objective (3) constraint for the nominal model 52 (and for the complete model set 52A) and the equation (19)/objective (4) constraint 54. It can be seen from FIG. 6 that the equation (20) objective function $M_d$ 50 meets the design constraints 52, 54 of equations (16), (19). When evaluated for the complete model set 52A, the equation (16)/objective (3) worst case gain constraint is met for the complete model set, except for a small number of models in the frequency range between 0.04-0.1 rad/s. If $\Delta C_e$ is set to $\Delta C_e$=5.5, instead of $\Delta C_e$=4.5 (see above discussion of equation (15A), then the equation (16)/objective (3) worst case gain constraint is met for all of the models in the complete model set. FIG. 7A shows the equation (20) objective function $M_d(s)$ and equation (2) predicted response of effect site concentration of analgesic agent $C_e$ to a step disturbance d of 10 units of $WAV_{CNS}$. FIG. 7B shows the corresponding rate of analgesic agent infusions $u_R$ (for the equation (20) objective in the FIG. 2 system) to a step disturbance d of 10 units of $WAV_{CNS}$.

Figure 8:
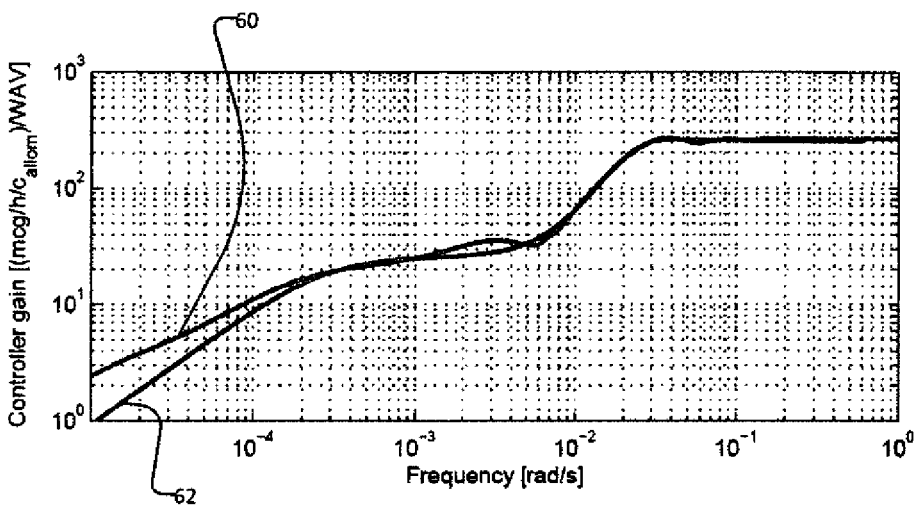
FIG. 8 is a Bode magnitude diagram of a frequency response of the FIG. 2 analgesic agent controller $K_R$ according to a particular embodiment.

After determining an objective function $M_d(s)$ that satisfies the design/control objectives (e.g. the equation (20) objective function $M_d(s)$), equation (10) may be used to design a full-order controller $K_R$. In the case of the one particular embodiment, evaluating equation (10) is based on knowledge of the pharmacokinetic-pharmacodynamic model ($G_{PKPD_R}$; e.g. the Minto et al. (or some other suitable) pharmacokinetic-pharmacodynamic model) and the sensitivity function of the nominal model describing the effect of the hypnotic agent on the $WAV_{CNS}$ ($S_P$). In the evaluation of equation (10), continuous time equivalents of the transfer functions may be used to avoid inverting systems with non-minimum phase zeros resulting from discretization. In one particular embodiment, the resulting controller $K_R$ is a continuous time 17$^{th}$ order transfer function with an internal delay of 77 seconds. The Bode magnitude diagram of the frequency response 60 of this controller $K_R$ is shown in FIG. 8

Because a 17$^{th}$ order controller is undesirably complex to use in some circumstances, a reduced order controller may be determined and used in some embodiments. In particular, in some embodiments, a reduced order controller $K_{R_{red}}(q^{-1})$ may be defined by minimizing the following model reduction criterion:

$$K_{R_{red}}(q^{-1}) = \underset{K_{red}}{\mathrm{argmin}} \sum_{\omega \in \Omega_k} M_{d_d}(e^{j\omega}) |K_{red}(e^{j\omega}) - K_{R_d}(e^{j\omega})| \Phi_{u_{id}}(e^{j\omega}) \quad (21)$$

where $M_{d_d}$ and $K_{R_d}$ represent zero order hold discretizations of $M_d$ and $K_R$ respectively, with sampling interval $T_s$=5 s. $K_{R_{red}}(q^{-1})$ is a discrete controller with $T_s$=5 s, $q^{-1}$ denotes the backward shift operator and $\Omega_k$ is a suitably selected frequency grid. In some embodiments, the frequency grid $\Omega_k$ may be determined by the signal $u_{id}$ used in the simulation experiment described below.

Equation (21) shows that in the case of one particular embodiment, the error between the full order controller $K_{R_d}$ and the reduced order controller $K_{R_{red}}$ is weighted by the objective function $M_d$—i.e. this error may be designed to be small at frequencies where the gain of the objective function $M_d$ is large. To maintain the controller characteristics and ensure zero gain at low frequencies, the reduced order discrete controller $K_{R_{red}}(q^{-1})$ may be designed, in some embodiments, to have a zero at q=1. In some such embodiments, a fixed term $K_{fix}(q^{-1})$ with a zero at q=1 may therefore be included in the reduced order controller. In some embodiments, the structure of $K_{red}(q^{-1})$ may be defined as:

$$K_{red}(q^{-1}) = \\ K_{fix}(q^{-1}) \frac{b_0 + b_1 q^{-1} + b_2 q^{-2}}{1 + a_1 q^{-1} + a_2 q^{-2}} = \frac{1 - q^{-1}}{1 - e^{-5/3600} q^{-1}} \frac{b_0 + b_1 q^{-1} + b_2 q^{-2}}{1 + a_1 q^{-1} + a_2 q^{-2}} \quad (22)$$

although it will be appreciated that other (e.g. higher order) structures may be used in the place of equation (22).

The optimization defined in equation (21) may be minimized using a simulation experiment. For example, in some embodiments, a simulation experiment may be constructed to minimize equation (21) where $u_{id}$ contains a plurality of periods of a pseudo random binary sequence (PRBS) signal of N samples. In one particular embodiment, a simulation experiment may be constructed to minimize equation (21) where $u_{id}$ contains four periods of a pseudo random binary signal of 4095 samples. The equation (22) parameters $b_0$, $b_1$, $b_2$, $a_1$ and $a_2$ may then identified using the output error structure. The resulting discrete time controller $K_{red}(q^{-1})$ is a 3rd order controller that contains no time delays. The Bode magnitude frequency response 62 of this reduced order controller $K_{red}(q^{-1})$ is compared to the Bode magnitude frequency response 60 of the full order controller in FIG. 8.

Figure 9:
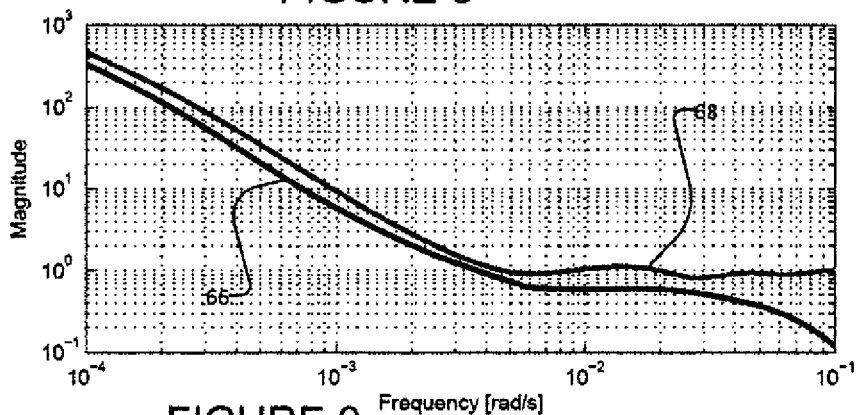
FIG. 9 is a Bode magnitude frequency response which demonstrates how a controller according to a particular embodiment may be made to satisfy robust stability criteria.

The robustness of the reduced order controller may be evaluated using equation (17). FIG. 9 shows the terms of the equation (17) inequality with the left hand side of the equation (17) inequality represented by plot 66 and the right hand side of the equation (17) inequality represented by plot 68. FIG. 9 shows the robustness criteria is satisfied by the reduced order controller $K_{red}(q^{-1})$.

As discussed above in relation to FIG. 2, feedforward filters $F_R$ and $F_{SP}$ may be used in some embodiments to shape various responses in some embodiments. In some embodiments, the feedforward filter $F_R$ may be designed such that $C_e$ rapidly achieves the steady state corresponding to $u_{R_{base}}$ (e.g. the user configurable baselines), assuming that the effect of feedback on this response is negligible (i.e. assuming $G_R=0$). Using a model-matching approach to design $F_R$, a reference model $M_{F_R}$ may be used to describe the desired dynamics, and the control objective may then be to design $F_R$ such that $C_e = G_{PKPD_R} F_R u_{R_{base}} = M_{F_R} u_{R_{base}}$. It follows that $$F_R = \frac{M_{F_R}}{G_{PKPD_R}}.$$

The Minto et al. pharmacokinetic-pharmacodynamic model $G_{PKPD_R}$ is a $4^{th}$ order model. In some embodiments, to limit the high frequency gain of the controller, the high frequency roll-off of $M_{F_R}$ may be set to be equal to or higher than the roll-off of $G_{PKPD_R}$. In some embodiments, designing a low order filter $F_R$, the structure of the reference model $M_{F_R}$ may be set to match the poles and zeros of $G_{PKPD_R}$. However, this is not necessary, and may restrict achievable performance.

In some embodiments, an approximate lower order filter may be identified using an experiment in simulation. In some embodiments, a reference model $M_{F_R}$ may be defined as:

$$M_{F_R} = \frac{G_{PKPD_R}(0)}{(15s+1)(30s+1)^2} \quad (22A)$$

In some embodiments, a weighting filter including an integrator may be included in the step where an approximate lower order filter is identified using an experiment in simulation, to assure the steady state gain (i.e. $F_R(\omega=0)$) at is close to unity. In some embodiments, the filter may be defined according to $$F_{id} = G_{PKPD_R} \frac{1200s+1}{s}.$$

In some embodiments, a plurality of periods of a pseudo random binary sequence (PRBS) signal of N samples with additional offset may be used for identification. In one particular embodiment, four periods of a PRBS signal of length 8191 samples with an additional offset of 0.01 may be used for identification. A relatively long period and/or a relatively large offset may increase the weight on low frequencies in the identification.

In some embodiments, a third order filter structure for $F_R$ may be identified using the output error structure. After identification, the filter gain may be adjusted to exactly match unity steady state gain. The response of the effect site concentration of analgesic agent $C_e$ for a step change in $u_{R_{base}}$ for the objective reference model $M_{F_R}$ as well as the achieved feedforward response ($G_{PKPD_R} F_R$) are shown in FIG. 10A. The results are so close that it is difficult to observe any difference between these responses at the scale of FIG. 10A. FIG. 10B also shows the input profile (i.e. the rate of infusion $u_R$ of analgesic agent) following a step change in $u_{R_{base}}$. This design of the feedforward filter $F_R$ leads to the administration of a feedforward bolus of analgesic agent, where most of the bolus dose is administered within a minute.

In some embodiments, the setpoint filter $F_{SP}$ may be designed to eliminate low frequency effects of setpoint changes to $WAV_{ref}$ on the rate of analgesic infusion. In one particular embodiments, this setpoint filter may have the form:

$$F_{SP} = \frac{1}{(300s+1)(180s+1)}$$

and may be implemented, in practice, by a discretized version of this filter with a sampling interval $T_s=5$ s.

FIGS. 11A-11C (collectively, FIG. 11) show example plots of various quantities in a combined hypnotic agent-analgesic agent control system 20 according to a particular embodiment of the type described herein to a strong unexpected stimulation d. In the embodiment illustrated in FIG. 11, the hypnotic agent comprises propofol and the analgesic agent comprises remifentanil. FIG. 11A shows two plots which include the measured $WAV_{CNS}$ 70 and the setpoint $WAV_{ref}$ 72. FIG. 11B shows the rate of propofol infusion $u_P$ 74 and the effect site propofol concentration 76 predicted by the so-called Schnider model. FIG. 11C shows the rate of remifentanil infusion 78, the user-configurable baseline reminfentanil infusion rate 80 and the Minto et al. predicted effect site remifentanil concentration 82. For the purposes of the FIG. 11 results, the measured DOH (in the form of $WAV_{CNS}$) as well as other indicators of depth of anesthesia (e.g. cardiovascular measures) were monitored by an anesthesiologist and were stable throughout the case. After half an hour the baseline remifentanil 80 was increased for a short period of time which resulted in an increase in the effect site concentration 82 of reminfentanil. After about 180 minutes strong nociceptive stimulation occurred, resulting in a spike in the measured $WAV_{CNS}$ 70. The control system 20 responded with a rapid increase in the infusion rate of remifentanil 78, leading to a relatively fast rejection of the nociceptive disturbance. After the disturbance, the control system 20 also returned the measured $WAV_{CNS}$ 70 to the setpoint $WAV_{ref}$ 72 with minimal overshoot.

Figure 12A:
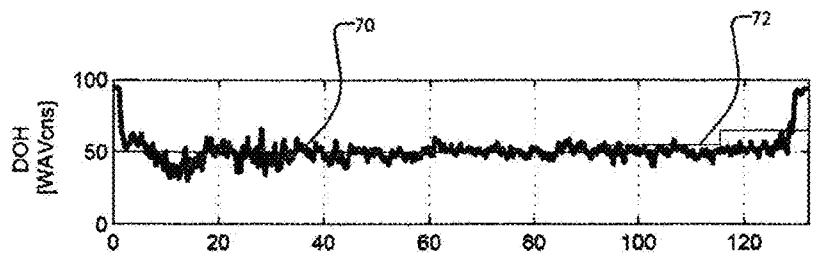
FIGS. 12A-12C (collectively, FIG. 12) show example plots (versus time) of various quantities in a combined hypnotic agent-analgesic agent control system according to a particular embodiment of the type described herein.
Figure 12B:
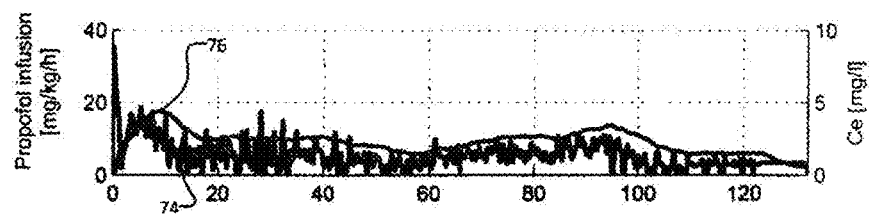
Figure 12C:
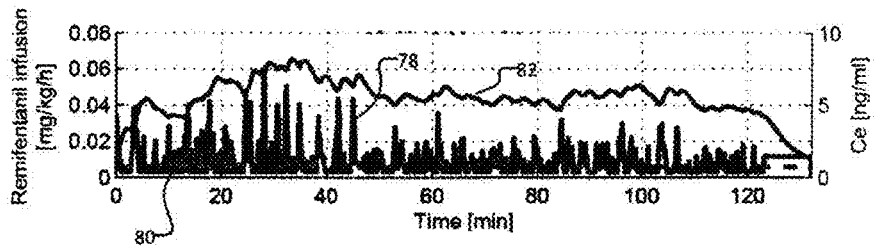

FIGS. 12A-12C (collectively, FIG. 12) show another example plots of various quantities in a combined hypnotic agent-analgesic agent control system 20 according to a particular embodiment of the type described herein to a strong unexpected stimulation d. In the embodiment illustrated in FIG. 12, the hypnotic agent comprises propofol and the analgesic agent comprises remifentanil. FIG. 12A shows two plots which include the measured $WAV_{CNS}$ 70 and the setpoint $WAV_{ref}$ 72. FIG. 12B shows the rate of propofol infusion $u_P$ 74 and the effect site propofol concentration 76 predicted by the model described by the so-called Schnider model. FIG. 12C shows the rate of remifentanil infusion 78, the user-configurable baseline reminfentanil infusion rate 80 and the Minto et al. predicted effect site remifentanil concentration 82. In the case shown in FIG. 12, variability in the measured $WAV_{CNS}$ 70 resulted in an increase in the predicted effect site concentration of remifentanil 82. After about 40 minutes, the variability of the measured $WAV_{CNS}$ 70 decreases and the control system 20 reduces the predicted effect site concentration of remifentanil 82 accordingly. The FIG. 12 control system 20 remains responsive to rapid increases in the measured $WAV_{CNS}$ 70—see, for example, after about 60 minutes and 85 minutes in the FIG. 12 plots.

Figure 13:
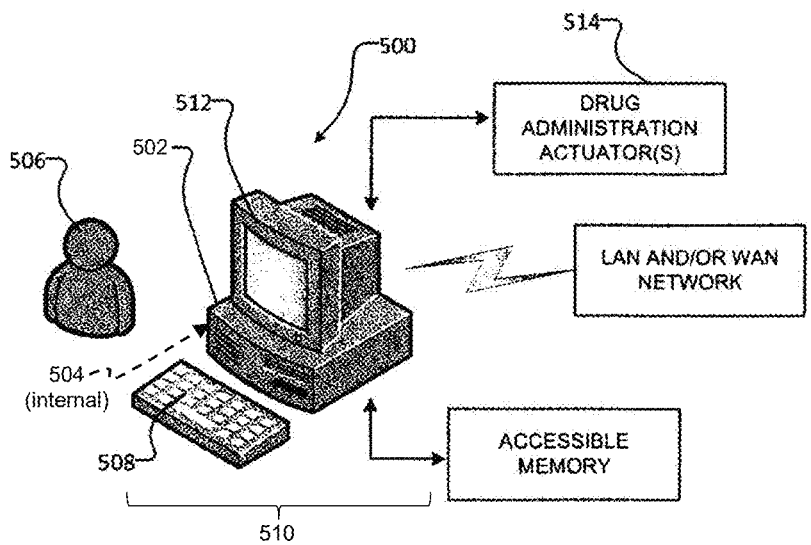
FIG. 13 is a schematic depiction of a system which may be used to implement any of the controllers and/or to perform any of the methods described herein and the steps of any of the methods described herein according to a particular embodiment.

FIG. 13 is a schematic depiction of a system 500 which may be used to implement any of the controllers and/or to perform any of the methods described herein and the steps of any of the methods described herein according to a particular embodiment. System 500 of the illustrated embodiment comprises one or more computers 502 which may comprise one or more processors 504 which may in turn execute suitable software (not expressly enumerated) accessible to processor(s) 504. When such software is executed by computer 502 (and in particular processor(s) 504), computer 502 and/or processor(s) 504 may implement any of the controllers and/or perform any of the methods described herein and the steps of any of the methods described herein. In the illustrated embodiment, computer 502 provides an optional user interface 510 for interaction with a user 506. From a hardware perspective, user interface 510 comprises one or more input devices 508 by which user 506 can input information to computer 502 and one or more output devices 512 by which information can be output to user 506 and one or more drug administration actuators 514 which can be used to administer drugs (e.g. an analgesic agent and a hypnotic agent) at controllable infusion rates. Various drug administration actuators 514 (e.g. electronically controllable injectors) are known to those skilled in the art and drug administration actuators 514 may comprise any such devices or systems. In general, input devices 508 and output devices 512 are not limited to those shown in the illustrated embodiment of FIG. 13. In general, input device 508 and output device 512 may comprise any suitable input and/or output devices suitable for interacting with computer 502. User interface 510 may also be provided in part by software when such software is executed by computer 502 and/or its processor(s) 504. In the illustrated embodiment, computer 502 is also connected to access data (and/or to store data) on accessible memory device 518. In the illustrated embodiment, computer 502 is also connected by communication interface 514 to a LAN and/or WAN network 516, to enable accessing data from networked devices (not shown) and/or communication of data to networked devices.

Input may be obtained by computer 502 via any of its input mechanisms, including, without limitation, by any input device 508, from accessible memory 518, from network 516 or by any other suitable input mechanism. The outputs may be output from computer 502 via any of its output mechanisms, including, without limitation, by any output device 512, to accessible memory 518, to network 516 or to any other suitable output mechanism. As discussed above, FIG. 13 is merely a schematic depiction of a particular embodiment of a computer-based system 500 suitable for implementing the methods described herein. Suitable systems are not limited to the particular type shown in the schematic depiction of FIG. 13 and suitable components (e.g. input and output devices) are not limited to those shown in the schematic depiction of FIG. 13.

The controllers and/or methods described herein may be implemented by computers comprising one or more processors and/or by one or more suitable processors, which may, in some embodiments, comprise components of suitable computer systems. By way of non-limiting example, such processors could comprise part of a computer-based automated contract valuation system. In general, such processors may comprise any suitable processor, such as, for example, a suitably configured computer, microprocessor, microcontroller, digital signal processor, field-programmable gate array (FPGA), other type of programmable logic device, pluralities of the foregoing, combinations of the foregoing, and/or the like. Such a processor may have access to software which may be stored in computer-readable memory accessible to the processor and/or in computer-readable memory that is integral to the processor. The processor may be configured to read and execute such software instructions and, when executed by the processor, such software may cause the processor to implement some of the functionalities described herein.

Certain implementations of the invention comprise computer processors which execute software instructions which cause the processors to implement a controller and/or perform a method of the invention. For example, one or more processors in a computer system may implement data processing steps in the controllers and/or methods described herein by executing software instructions retrieved from a program memory accessible to the processors. The invention may also be provided in the form of a program product. The program product may comprise any medium which carries a set of computer-readable signals comprising instructions which, when executed by a data processor, cause the data processor to implement a controller and/or execute a method of the invention. Program products according to the invention may be in any of a wide variety of forms. The program product may comprise, for example, physical (non-transitory) media such as magnetic data storage media including floppy diskettes, hard disk drives, optical data storage media including CD ROMs, DVDs, electronic data storage media including ROMs, flash RAM, or the like. The instructions may be present on the program product in encrypted and/or compressed formats.

Where a component (e.g. a software module, controller, processor, assembly, device, component, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Closed loop controllers according to the embodiments described herein exhibit a number of advantageous features which are novel in relation to the prior art. Such controllers implement a method which controls a first rate of infusion of a hypnotic agent $u_P$ into a subject and a second rate of infusion of an analgesic agent $u_R$ into a subject. Such methods involve: receiving, at a computer processor, a measure representative of a depth of hypnosis (a DOH measure) of the subject; and determining by the computer processor, a first control signal (or value) for each of first series of time steps to control a first rate of infusion of a hypnotic agent $u_P$ into a subject and determining a second control signal (or value) for each of a second series of time steps to control a second rate of infusion of an analgesic agent $u_R$ into the subject, wherein determining the first control signal and determining the second control signal are both based on the DOH measure. Such methods also involve outputting, from the computer processor, the first control signal to a hypnotic agent injector at each of the first series of time steps, to thereby control the hypnotic agent injector to inject the hypnotic agent into the subject at the first rate of infusion of the hypnotic agent $u_P$ and outputting the second control signal to an analgesic agent injector at each of the second series of time steps, to thereby control the analgesic agent injector to inject the analgesic agent into the subject at the second rate of infusion of the analgesic agent $u_R$.

In some embodiments, the controller is designed such that the response of the controller for the analgesic agent is dominant at higher frequencies and the response of the controller for the hypnotic agent is dominant at lower frequencies. This recognition may be observed by several characteristics of the controllers of the various embodiments described herein. In some embodiments, the first series of time steps (for which the first control signal is determined and output) and the second series of time steps (for which the second control signal is determined and output) are the same as one another.

In some embodiments, a number of definitions are useful to describe the characteristics of the control systems and methods. As discussed above: the variable $u_P$ represents the first control signal for controlling the first rate of infusion of the hypnotic agent (which may be described in terms of the units mcg/kg/min or µg/kg/min); the variable $u_R$ represents the second control signal for controlling the second rate of infusion of the analgesic agent (which may be measured in units of ng/kg/min); and the variables $WAV_{ref}$ and $WAV_{CNS}$ are variables representative of a desired depth of hypnosis and a measured depth of hypnosis on a particular index (e.g. in a unitless range of 0-100). We may then define: $S_P(\omega)$ to denote the power spectral density of the first control signal $u_P$ for controlling the first rate of infusion of hypnotic agent at frequencies $\omega$; $S_R(\omega)$ to denote the power spectral density of the second control signal $u_R$ for controlling the second rate of infusion of analgesic agent at frequencies $\omega$; and $S_E(\omega)$ to denote the power spectral density of the DOH error signal (e.g. $WAV_{ref}-WAV_{CNS}$ (see FIG. 2) or some other measure of the error between the measured DOH and the reference DOH) at frequencies $\omega$. It will be appreciated that where $u_P$, $u_R$, $WAV_{ref}$ and $WAV_{CNS}$ have the units referred to above, then the respective power spectral densities $S_P(\omega)$, $S_R(\omega)$ and $S_E(\omega)$ will have the respective units $$\frac{(\mu g'kg'min)^2}{rad/s},$$

$$\frac{(ng'kg'min)^2}{rad/s},$$

and $$\frac{(DOH\ index)^2}{rad/s}.$$

We may then further define amplifications of the spectral densities as follows:

$$A_P(\omega) = \frac{S_P(\omega)}{S_E(\omega)}$$

may be defined to be the amplification of the spectral density of the first control signal $S_P(\omega)$ relative to the spectral density of the DOH error $S_E(\omega)$; and $$A_R(\omega) = \frac{S_R(\omega)}{S_E(\omega)}$$

may be defined to be the amplification of the spectral density of the second control signal $S_R(\omega)$ relative to the spectral density of the DOH error $S_E(\omega)$. It will be appreciated that where $u_P$, $u_R$, $WAV_{ref}$ and $WAV_{CNS}$ have the units referred to above, then the respective spectral density amplifications $A_P(\omega)$ and $A_R(\omega)$ will have the respective units $$\frac{(\mu g'kg'min)^2}{(DOH\ index)^2} \text{ and } \frac{(ng'kg'min)^2}{(DOH\ index)^2}.$$

We may then define an amplification integral over a frequency band $w=[\omega_1, \omega_2]$ as follows:

$$I_P(w) = \frac{1}{\pi} \int_{\omega_1}^{\omega_2} A_P(\omega) d\omega$$

may be defined to the integral of the amplification $A_P(\omega)$ of the spectral density of the first control signal $S_P(\omega)$; and $$I_R(w) = \frac{1}{\pi} \int_{\omega_1}^{\omega_2} A_R(\omega) d\omega$$

may be defined to the integral of the amplification $A_R(\omega)$ of the spectral density of the second control signal $S_R(\omega)$. It will be appreciated that where $u_P$, $u_R$, $WAV_{ref}$ and $WAV_{CNS}$ have the units referred to above, then the respective amplification integrals $I_P(\omega)$ and $I_R(\omega)$ will have the respective units $$\left[\frac{(\mu g'kg'min)^2}{(DOH\ index)^2} \cdot \frac{rad}{s}\right] \text{ and } \left[\frac{(ng'kg'min)^2}{(DOH\ index)^2} \cdot \frac{rad}{s}\right].$$

It will be appreciated that the amplification integral(s) $I_P$ and/or $I_R$ over a frequency band $w=[\omega_1, \omega_2]$ are representative of a strength of the corresponding amplification(s) $A_P$ and/or $A_R$ over the frequency band $w=[\omega_1, \omega_2]$. It will be observed that if $S_P(\omega)$ is the power spectral density of the output of a linear filter H fed by a signal with a power spectral density of $S_E(\omega)$, then these two power spectral densities are related according to $S_P(\omega)=|H(j\omega)|^2 S_E(\omega)$. It will be further appreciated that where $\omega_1=0$ rad/s and $\omega_2=\pi$ rad/s, then the amplification integral(s) $I_P$ and/or $I_R$ over the frequency band $w=[\omega_1, \omega_2]$ correspond to the square of the 2-norm of the linear filter $H(j\omega)$.

In some embodiments, the response of the controller for the analgesic agent is dominant at higher frequencies relative to the response of the controller for the hypnotic agent and the response of the controller for the hypnotic agent is dominant at lower frequencies relative to the response of the controller for the analgesic agent. These features advantageously permit fast blunting or suppression of any nociceptive reaction without interfering unduly with the hypnotic control loop.

For example, using the definitions set out above, in some embodiments, we may define a low frequency range of interest for the context of clinical anesthesia to be $w_1=$ [0.0001 rad/s, 0.006 rad/sec] and a high frequency range of interest for the context of clinical anesthesia to be $w_2=$[0.006 rad/s, 0.08 rad/s]. In some embodiments, a ratio of $I_P(w_2)/I_P(w_1)$ (i.e. a ratio of the integral of the amplification $A_P(\omega)$ of the spectral density of the first (hypnotic agent) control signal $S_P(\omega)$ over the high frequency range $w_2$ to the integral of the amplification $A_P(\omega)$ over the low frequency range $w_1$) is less than $I_R(w_2)/I_R(w_1)$ (i.e. a ratio of the integral of the amplification $A_R(\omega)$ of the spectral density of the second (analgesic agent) control signal $S_R(\omega)$ over the high frequency range $w_2$ to the integral of the amplification $A_R(\omega)$ over the low frequency range $w_1$).

As another example, in some embodiments, the ratio of $I_P(w_2)/I_P(w_1)$ is less than 20 ($I_P(w_2)/I_P(w_1)<20$). In some embodiments, the ratio $I_P(w_2)/I_P(w_1)$ is less than 10 ($I_P(w_2)/I_P(w_1)<10$). In some embodiments, the ratio $I_P(w_2)/I_P(w_1)$ is less than 2 ($I_P(w_2)/I_P(w_1)<2$). In some embodiments, the ratio $I_R(w_2)/I_R(w_1)$ is greater than or equal to 20 ($I_R(w_2)/I_R(w_1)\geq20$). In some embodiments, the ratio $I_R(w_2)/I_R(w_1)$ is greater than or equal to 100 ($I_R(w_2)/I_R(w_1)\geq100$). In some embodiments, the ratio $I_R(w_2)/I_R(w_1)$ is greater than or equal to 200 ($I_R(w_2)/I_R(w_1)\geq200$).

As another example, in some embodiments, the amplification integral $I_P(w_1)$ of the amplification $A_P(\omega)$ of the spectral density of the first (hypnotic agent) control signal $S_P(\omega)$ over the low frequency range $w_1$ is greater than or equal to 0.2 (i.e. $I_P(w_1)\geq0.2$) where the control variable $u_P$ and the DOH error signal (e.g. $WAV_{ref}-WAV_{CNS}$) have the units described above. In some embodiments, $I_P(w_1)\geq2.0$ where the control variable $u_P$ and the DOH error signal (e.g. $WAV_{ref}-WAV_{CNS}$) have the units described above. In some embodiments, $P_P(w_1)\geq5.0$ where the control variable $u_P$ and the DOH error signal (e.g. $WAV_{ref}-WAV_{CNS}$) have the units described above. In some embodiments, the amplification integral $I_R(w_2)$ of the amplification $A_R(\omega)$ of the spectral density of the second (analgesic agent) control signal $S_R(\omega)$ over the high frequency range $w_2$ is greater than or equal to 1 (i.e. $P_R(w_2)\geq1$) where the control variable $u_R$ and the DOH error signal (e.g. $WAV_{ref}-WAV_{CNS}$) have the units described above. In some embodiments, $P_R(w_2)\geq2.5$ where the control variable $u_R$ and the DOH error signal (e.g. $WAV_{ref}-WAV_{CNS}$) have the units described above. In some embodiments, $P_R(w_2)\geq10$ where the control variable $u_R$ and the DOH error signal (e.g. $WAV_{ref}-WAV_{CNS}$) have the units described above.

In some embodiments, determining the analgesic agent control signal $\underline{u_R}$ comprises implementing a controller having an analgesic agent amplification $A_R(\omega)$ of less than $-3$ dB in circumstances where the DOH error (e.g. $WAV_{ref}-WAV_{CNS}$) varies at a frequency of less than or equal to $\omega=10^{-5}$ rad/s (i.e. $A_R(\omega)<-3$ dB for $\omega\leq10^{-5}$ rad/s), where analgesic agent amplification $A_R(\omega)$ is equal to the power spectral density $S_R(\omega)$ of the second (analgesic agent) control signal over the power spectral density $S_E(\omega)$ of the DOH error, the control variable $u_R$ and the DOH error signal (e.g. $WAV_{ref}-WAV_{CNS}$) have the units described above. In some embodiments, $A_R(\omega)<-3$ dB for variation in DOH error at frequencies of less than $$\omega \leq 10^{-5}\frac{\text{rad}}{\text{s}},$$

and $A_R(\omega)<-10$ dB for variation in DOH error at frequencies of less than $\omega\leq10^{-6}$ rad/s, where analgesic agent amplification $A_R(\omega)$ is equal to the power spectral density $S_R(\omega)$ of the second (analgesic agent) control signal over the power spectral density $S_E(\omega)$ of the DOH error, the control variable $u_R$ and the DOH error signal (e.g. $WAV_{ref}-WAV_{CNS}$) have the units described above. In some embodiments, $A_R(\omega)<-3$ dB for variation in DOH error at frequencies of less than $$\omega \leq 10^{-5}\frac{\text{rad}}{\text{s}},$$

and $A_R(\omega)<-23$ dB for variation in DOH error at frequencies of less than $\omega\leq10^{-6}$ rad/s, where analgesic agent amplification $A_R(\omega)$ is equal to the power spectral density $S_R(\omega)$ of the second (analgesic agent) control signal over the power spectral density $S_E(\omega)$ of the DOH error, the control variable $u_R$ and the DOH error signal (e.g. $WAV_{ref}-WAV_{CNS}$) have the units described above.

INTERPRETATION OF TERMS

Unless the context clearly requires otherwise, throughout the description and the claims:
- "comprise", "comprising", and the like are to be construed in an inclusive sense, as opposed to an exclusive or exhaustive sense; that is to say, in the sense of "including, but not limited to";
- "connected", "coupled", or any variant thereof, means any connection or coupling, either direct or indirect, between two or more elements; the coupling or connection between the elements can be physical, logical, or a combination thereof; elements which are integrally formed may be considered to be connected or coupled;
- "herein", "above", "below", and words of similar import, when used to describe this specification, shall refer to this specification as a whole, and not to any particular portions of this specification;
- "or", in reference to a list of two or more items, covers all of the following interpretations of the word: any of the items in the list, all of the items in the list, and any combination of the items in the list;
- the singular forms "a", "an", and "the" also include the meaning of any appropriate plural forms.

in different directions, and/or be offset from each other by a space and/or an angle.

Embodiments of the invention may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs")). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a computer system for a device may implement methods as described herein by executing software instructions in a program memory accessible to the processors.

Processing may be centralized or distributed. Where processing is distributed, information including software and/or data may be kept centrally or distributed. Such information may be exchanged between different functional units by way of a communications network, such as a Local Area Network (LAN), Wide Area Network (WAN), or the Internet, wired or wireless data links, electromagnetic signals, or other data communication channel.

For example, while processes or blocks are presented in a given order, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

In addition, while elements are at times shown as being performed sequentially, they may instead be performed simultaneously or in different sequences. It is therefore intended that the following claims are interpreted to include all such variations as are within their intended scope.

Embodiments of the invention may also be provided in the form of a program product. The program product may comprise any non-transitory medium which carries a set of computer-readable instructions which, when executed by a data processor, cause the data processor to execute a method of the invention. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or preprogrammed chips (e.g., EEPROM semiconductor chips), nanotechnology memory, or the like. The computer-readable signals on the program product may optionally be compressed or encrypted.

In some embodiments, the invention may be implemented in software. For greater clarity, "software" includes any instructions executed on a processor, and may include (but is not limited to) firmware, resident software, microcode, and the like. Both processing hardware and software may be centralized or distributed (or a combination thereof), in whole or in part, as known to those skilled in the art. For example, software and other modules may be accessible via local memory, via a network, via a browser or other application in a distributed computing context, or via other means suitable for the purposes described above.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Where a record, field, entry, and/or other element of a database is referred to above, unless otherwise indicated, such reference should be interpreted as including a plurality of records, fields, entries, and/or other elements, as appropriate. Such reference should also be interpreted as including a portion of one or more records, fields, entries, and/or other elements, as appropriate. For example, a plurality of "physical" records in a database (i.e. records encoded in the database's structure) may be regarded as one "logical" record for the purpose of the description above and the claims below, even if the plurality of physical records includes information which is excluded from the logical record.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

While a number of exemplary aspects and embodiments have been discussed above, those of skill in the art will recognize certain modifications, permutations, additions and sub-combinations thereof. For example:

In some embodiments, feedback is provided by a measure indicative of the depth of hypnosis (DOH) of a patient. In some of the particular embodiments described above, this measure/indicia of DOH is provided by the $WAV_{CNS}$ index generated by a NeuroSENSE™ monitor provided by NeuroWave Systems Inc. of Cleveland Heights, Ohio. This is not necessary. In some embodiments, other suitable DOH measure(s)/indicia could be used to provide feedback to the control system/method. Such other suitable DOH measure(s)/indicia could be used in addition to or in the alternative to provide feedback to the control system/method.

In general, the description set out above describes specific embodiments of methods for designing controllers that achieve a set of design objectives. In some embodiments, different control design techniques and/or different control design starting points may be used to achieve the design objectives. For example, such control objectives may be achievable using model predictive control, non-linear control, adaptive control, rule-based control and/or the like.

Some of the above-described embodiments achieve a control solution that is a robust control solution (to inter-patient variability) using specific model set(s) and unstructured uncertainty, which may lead to equation (17), for example. This is not necessary. In some embodiments, controllers may be designed to be robustly stable to inter-patient variability using different model(s), different model structure, different controller design and/or the like. In some embodiments, any model/description that quantifies variability over a definable subset of the population may be used. For example, such models may comprise linear models with structured uncertainty, unstructured uncertainty and/or parametric uncertainty, non-linear models, non-parametric models and/or the like. Provided that the model(s) quantify variability over a definable subset of the population, any suitable technique(s) can be used to design a controller or to otherwise ensure that the controller achieves robust stability to inter-patient variability. For example, such technique(s) may include: robust model-predictive control, robust non-linear control, robust adaptive control, robust rule-based control and/or the like. In some embodiments, robustness can be taken into account or evaluated a posteriori using analytical robustness criteria (e.g. like equation (17)), using suitable simulation (e.g. Monte Carlo probability based simulation) and/or the like.

Some of the above-described embodiments implement a controller where the predicted analgesic effect site concentration $C_e$ increases at least roughly proportionally to a step increase in the measure representative of depth of hypnosis (DOH) of the subject (e.g. $WAV_{CNS}$). Some of the above-described embodiments achieve this objective use model-reference control by forcing the closed loop transfer function equal to $M_d$—see discussion of equations (8)-(10) above. This is not necessary. In some embodiments, this control objective can be achieved using model predictive control, non-linear control, adaptive control, rule-based control and/or the like. In some embodiments, this objective can be achieved by tuning the controller (e.g. manually, by performance evaluation using simulation, using numerical optimization and/or the like).

Some of the above-described embodiments implement a controller where the analgesic agent amplification $A_R(\omega)$ is less than −3 dB in circumstances where DOH error (i.e. a difference between the reference depth of hypnosis $DOH_{ref}$ and the measure representative of depth of hypnosis (DOH) of the subject) varies at low frequencies. Some of the above-described embodiments achieve this objective using a linear control technique by providing a zero in the controller (i.e. $K_R(0)=0$). In some embodiments, this control objective can be achieved using model predictive control, non-linear control, adaptive control, rule-based control and/or the like.

Some of the above-described embodiments implement a controller where the rate of infusion of the analgesic agent $u_R$ is greater than a lower bound $u_{Rbase}$ for all time steps. Some of the above-described embodiments achieve this objective using a constraint imposed on the controller. In some embodiments, this lower bound on the rate of infusion of the analgesic agent $u_R$ could be integrated into the controller design. Some of the above-described embodiments implement a controller where the average control signal that controls the rate of infusion of the analgesic agent $u_R$ is bound in response to noise in the measure representative of depth of hypnosis (DOH) of the subject (e.g. $WAV_{CNS}$)—see, for example, equation (16) above. In some embodiments, this objective could be achieved by directly imposing a hard bound or constraint. In some embodiments, this control objective can be achieved using model predictive control, non-linear control, adaptive control, rule-based control and/or the like.

Some of the above-described embodiments implement a controller which is robustly stable in the measure representative of the depth of hypnosis (DOH) of the subject (e.g. $WAV_{CNS}$) despite non-linear interaction between the hypnotic agent and the analgesic agent using the so-called small gain theorem. In some embodiments, other techniques could be used to analyze the stability of non-linear systems. Non-limiting examples of such non-linear stability analysis techniques include Lyapunov functions, passivity results and/or the like. In some embodiments, this control objective can be achieved using model predictive control, non-linear control, adaptive control, rule-based control and/or the like.

It is therefore intended that the following appended aspects and/or claims and/or aspects and/or claims hereafter introduced are interpreted to include all such modifications, permutations, additions and sub-combinations as are within their true spirit and scope.

The invention claimed:

1. A method for controlling a first rate of infusion of a hypnotic agent uP into a subject and a second rate of infusion of an analgesic agent uR into the subject, the method comprising:

receiving, at a computer processor, a measure representative of a depth of hypnosis (DOH) of the subject is selected from a group of indices consisting of a WAVCNS index or a BIS index;

determining, by the computer processor, a first control signal (or value) for each of a first series of time steps to control the first rate of infusion of a hypnotic agent $u_P$ into the subject and determining a second control signal (or value) for each of a second series of time steps to control the second rate of infusion of the analgesic agent $u_R$ into the subject, wherein determining the first control signal and determining the second control signal are both based on the measure representative of the depth of hypnosis; and outputting, from the computer processor, the first control signal to a hypnotic agent administration actuator at each of the first series of time steps, to thereby control the hypnotic agent administration actuator to inject the hypnotic agent into the subject at the first rate of infusion of the hypnotic agent $u_P$ and outputting the second control signal to an analgesic agent administration actuator at each of the second series of time steps, to thereby control the analgesic agent administration actuator to inject the analgesic agent into the subject at the second rate of infusion of the analgesic agent $u_R$;

wherein the first series of time steps is the same as the second series of time steps.

2. The method of claim 1, wherein determining the first control signal and determining the second control signal comprise determining the first and second control signals, such that when the first and second control signals are output to the hypnotic agent administration actuator and the analgesic agent administration actuator, the first and second control signals cause the hypnotic agent administration actuator and the analgesic agent administration actuator to inject the hypnotic agent into the subject at the first rate of infusion of the hypnotic agent $u_P$ and to inject the analgesic agent into the subject at the second rate of infusion of the analgesic agent $u_R$ to thereby cause the measure representative of depth of hypnosis (DOH) of the subject to track a reference depth of hypnosis $DOH_{ref}$.

3. AThe method of claim 2, wherein a response of the second (analgesic agent) control signal to a DOH error (between the reference depth of hypnosis $DOH_{ref}$ and the measure representative of the DOH) is dominant at higher frequencies relative to a response of the controller for the first (hypnotic agent) control signal to the DOH error.

4. The method of claim 3, wherein a response of the controller for the first (hypnotic agent) control signal to a DOH error (between the reference depth of hypnosis $DOH_{ref}$ and the measure representative of the DOH) is dominant at lower frequencies relative to a response of the controller for the second (analgesic agent) control signal to the DOH error.

5. The method of claim 3, wherein determining the second control signal comprises implementing a second controller, the second controller having an analgesic agent amplification $A_R(\omega)$ of less than −3 dB in circumstances where DOH error (i.e. a difference between the reference depth of hypnosis $DOH_{ref}$ and the measure representative of depth of hypnosis (DOH) of the subject) varies at a frequency of less than or equal to $\omega=10^{-5}$ rad/s (i.e. $A_R(\omega) \leq -3$ dB for $\omega \leq 10^{-5}$ rad/s.), where analgesic agent amplification $A_R(\omega)$ is equal to the power spectral density $S_R(\omega)$ of the second (analgesic agent) control signal over the power spectral density $S_E(\omega)$ of the DOH error, the second (analgesic agent) control signal is expressed in the units ng/kg/min, the DOH error (between the reference depth of hypnosis $DOH_{ref}$ and the measure representative of the DOH) is expressed in units of a DOH index and frequencies are expressed in units of rad/s.

6. The method of claim 2, wherein a response of the controller for the first (hypnotic agent) control signal to a DOH error (between the reference depth of hypnosis $DOH_{ref}$ and the measure representative of the DOH) is dominant at lower frequencies relative to a response of the controller for the second (analgesic agent) control signal to the DOH error.

7. The method of Claim 2, wherein determining the second control signal comprises implementing a second controller, the second controller having an analgesic agent amplification $A_R(\omega)$ of less than −3 dB in circumstances where DOH error (i.e. a difference between the reference depth of hypnosis $DOH_{ref}$ and the measure representative of depth of hypnosis (DOH) of the subject) varies at a frequency of less than or equal to $\omega=10^{-5}$ rad/s (i.e. $A_R(\omega) \leq -3$ dB for $\omega \leq 10^{-5}$ rad/s.), where analgesic agent amplification $A_R(\omega)$ is equal to the power spectral density $S_R(\omega)$ of the second (analgesic agent) control signal over the power spectral density $S_E(\omega)$ of the DOH error, the second (analgesic agent) control signal is expressed in the units ng/kg/min, the DOH error (between the reference depth of hypnosis $DOH_{ref}$ and the measure representative of the DOH) is expressed in units of a DOH index and frequencies are expressed in units of rad/s.

8. The method of claim 1, wherein:
a low frequency range of interest for the context of clinical anesthesia is $w_1=[0.0001$ rad/s, $0.006$ rad/sec] and a high frequency range of interest for the context of clinical anesthesia is $w_2=[0.006$ rad/s, $0.08$ rad/s]; and
a ratio of an amplification integral of the hypnotic agent amplification $A_P(\omega)$ over the high frequency range $w_2$ to the amplification integral of the hypnotic agent amplification $A_P(\omega)$ over the low frequency range $w_1$ (i.e. $I_P(w_2)/I_P(w_1)$) is less than a ratio of the amplification integral of the analgesic agent amplification $A_R(\omega)$ over the high frequency range $w_2$ to the amplification integral of the amplification $A_R(\omega)$ over the low frequency range $w_1$ (i.e. $I_R(w_2)/I_R(w_1)$);
where the hypnotic agent amplification $A_P(\omega)$ is equal to the power spectral density $S_P(\omega)$ of the first (hypnotic agent) control signal over the power spectral density $S_E(\omega)$ of the DOH error and the analgesic agent amplification $A_R(\omega)$ is equal to the power spectral density $S_R(\omega)$ of the second (analgesic agent) control signal over the power spectral density $S_E(\omega)$ of the DOH error.

9. The method of Claim 1, wherein:
a low frequency range of interest for the context of clinical anesthesia is $w_1=[0.0001$ rad/s, $0.006$ rad/sec] and a high frequency range of interest for the context of clinical anesthesia is $w_2=[0.006$ rad/s, $0.08$ rad/s]; and
a ratio of an amplification integral of the hypnotic agent amplification $A_P(\omega)$ over the high frequency range $w_2$ to the amplification integral of the hypnotic agent amplification $A_P(\omega)$ over the low frequency range $w_1$ is less than 20 (i.e. $I_P(w_2)/I_P(w_1)<20$);

where the hypnotic agent amplification $A_P(\omega)$ is equal to the power spectral density $S_P(\omega)$ of the first (hypnotic agent) control signal over the power spectral density $S_E(\omega)$ of the DOH error.

10. The method of Claim 1, wherein:
a low frequency range of interest for the context of clinical anesthesia is $w_1=[0.0001$ rad/s, $0.006$ rad/sec] and a high frequency range of interest for the context of clinical anesthesia is $w_2=[0.006$ rad/s, $0.08$ rad/s]; and
a ratio of an amplification integral of the analgesic agent amplification $A_R(\omega)$ over the high frequency range $w_2$ to the amplification integral of the analgesic agent amplification $A_R(\omega)$ over the low frequency range $w_1$ is greater than or equal to 20 (i.e. $I_R(w_2)/I_R(w_1) \geq 20$);
where the analgesic agent amplification $A_R(\omega)$ is equal to the power spectral density $S_R(\omega)$ of the second (analgesic agent) control signal over the power spectral density $S_E(\omega)$ of the DOH error.

11. The method of Claim 1, wherein:
a low frequency range of interest for the context of clinical anesthesia is $w_1=[0.0001$ rad/s, $0.006$ rad/sec] and a high frequency range of interest for the context of clinical anesthesia is $w_2=[0.006$ rad/s, $0.08$ rad/s]; and
an amplification integral $I_P(w_1)$ of a hypnotic agent amplification $A_P(\omega)$ over the low frequency range $w_1$ is greater than or equal to 0.2 (i.e. $I_P(w_1) \geq 0.2$), where the hypnotic agent amplification $A_P(\omega)$ is equal to the power spectral density $S_P(\omega)$ of the first (hypnotic agent) control signal over the power spectral density $S_E(\omega)$ of the DOH error, the first (hypnotic agent) control signal is expressed in the units mcg/kg/min, the DOH error (between the reference depth of hypnosis $DOH_{ref}$ and the measure representative of the DOH) is expressed in units of a DOH index and frequencies are expressed in units of rad/s.

12. The method of Claim 1, wherein:
a low frequency range of interest for the context of clinical anesthesia is $w_1=[0.0001$ rad/s, $0.006$ rad/sec] and a high frequency range of interest for the context of clinical anesthesia is $w_2=[0.006$ rad/s, $0.08$ rad/s]; and
an amplification integral $I_R(w_2)$ of an analgesic agent amplification $A_R(\omega)$ over the high frequency range $w_2$ is greater than or equal to 1 (i.e. $I_R(w_2) \geq 1$), where the analgesic agent amplification $A_R(\omega)$ is equal to the power spectral density $S_R(\omega)$ of the second (analgesic agent) control signal over the power spectral density $S_E(\omega)$ of the DOH error, the second (analgesic agent) control signal is expressed in the units ng/kg/min, the DOH error (between the reference depth of hypnosis $DOH_{ref}$ and the measure representative of the DOH) is expressed in units of a DOH index and frequencies are expressed in units of rad/s.

13. The method of Claim 1, wherein determining the second control signal comprises determining the second control signal, such that when the second control signal is output to the analgesic agent administration actuator, the second control signal causes the analgesic agent administration actuator to inject the analgesic agent into the subject at the second rate of infusion of the analgesic agent $u_R$ which causes a predicted analgesic effect site concentration $C_e$ to increase by an amount which is proportional, to within +/−10%, to a step increase in the measure representative of depth of hypnosis (DOH) of the subject.

14. The of Claim 1, wherein determining the second control signal comprises determining the second control signal, such that when the second control signal is output to the analgesic agent administration actuator, the second control signal causes the analgesic agent administration actuator to inject the analgesic agent into the subject at the second rate of infusion of the analgesic agent $u_R$ which is greater than a lower bound $u_{Rbase}$ for all time steps in the second series of time steps.

15. The method of Claim 14, wherein determining the second control signal comprises bounding an average, over time, of the second control signal in response to noise in the measure representative of depth of hypnosis (DOH) of the subject.

16. The method of Claim 14, wherein determining the second control signal comprises implementing a second controller subject to the constraint of equation (16) described above.

17. The method of Claim 1, wherein determining the first control signal and determining the second control signal comprise determining the first and second control signals, such that when the first and second control signals are output to the hypnotic agent administration actuator and the analgesic agent administration actuator, the first and second control signals cause the hypnotic agent administration actuator and the analgesic agent administration actuator to inject the hypnotic agent into the subject at the first rate of infusion of the hypnotic agent $u_P$ and to inject the analgesic agent into the subject at the second rate of infusion of the analgesic agent $u_R$ to thereby implement robust stability of the measure representative of the depth of hypnosis (DOH) of the subject despite non-linear interaction between the hypnotic agent and the analgesic agent.

18. The method of Claim 17, wherein determining the second control signal comprises implementing a second controller subject to the constraint of equation (19) described above.

19. The method of Claim 1, wherein determining the first control signal and determining the second control signal comprise determining the first and second control signals, such that when the first and second control signals are output to the hypnotic agent administration actuator and the analgesic agent administration actuator, the first and second control signals cause the hypnotic agent administration actuator and the analgesic agent administration actuator to inject the hypnotic agent into the subject at the first rate of infusion of the hypnotic agent $u_P$ and to inject the analgesic agent into the subject at the second rate of infusion of the analgesic agent $u_R$ to thereby implement robust stability of the measure representative of the depth of hypnosis (DOH) of the subject despite inter-patient variability over an entire definable subset of the population.

20. The method of Claim 19, wherein determining the second control signal comprises implementing a second controller subject to the constraint of equation (17) described above.

* * * * *